US009443521B1

(12) United States Patent
Olguin Olguin et al.

(10) Patent No.: US 9,443,521 B1
(45) Date of Patent: Sep. 13, 2016

(54) METHODS FOR AUTOMATICALLY ANALYZING CONVERSATIONAL TURN-TAKING PATTERNS

(71) Applicant: Sociometric Solutions, Inc., Boston, MA (US)

(72) Inventors: Daniel Olguin Olguin, Boston, MA (US); Tuomas Jaanu, Charlestown, MA (US); Maegen Demko, Brighton, MA (US)

(73) Assignee: Sociometric Solutions, Inc., Boston, MA (US)

( * ) Notice: Subject to any disclaimer, the term of this patent is extended or adjusted under 35 U.S.C. 154(b) by 163 days.

(21) Appl. No.: 14/172,872

(22) Filed: Feb. 4, 2014

Related U.S. Application Data

(60) Provisional application No. 61/764,911, filed on Feb. 14, 2013.

(51) Int. Cl.
*G10L 15/00* (2013.01)
*G10L 17/00* (2013.01)

(52) U.S. Cl.
CPC .................................... *G10L 17/00* (2013.01)

(58) Field of Classification Search
None
See application file for complete search history.

(56) References Cited

U.S. PATENT DOCUMENTS

| 8,706,827 | B1 * | 4/2014 | Noble | G10L 13/027 704/9 |
| 8,843,372 | B1 * | 9/2014 | Isenberg | G10L 17/26 704/250 |
| 2004/0172252 | A1 * | 9/2004 | Aoki | H04M 3/564 704/270 |
| 2008/0111832 | A1 * | 5/2008 | Emam | G02B 27/017 345/633 |
| 2011/0092337 | A1 | 4/2011 | Srinivasan et al. | |
| 2011/0201959 | A1 | 8/2011 | Price et al. | |
| 2013/0013014 | A1 | 1/2013 | Donnelly et al. | |
| 2013/0039498 | A1 * | 2/2013 | Adachi | A61B 5/04845 381/56 |
| 2014/0081637 | A1 * | 3/2014 | Wren | G10L 19/018 704/246 |

(Continued)

FOREIGN PATENT DOCUMENTS

| KR | 10-2008-0087002 | 9/2008 |
| WO | WO 2007/070298 A1 | 6/2007 |
| WO | WO2014/197176 | 12/2014 |

OTHER PUBLICATIONS

Adar, E., "Guess: a language and interface for graph exploration," *CHI '06 Proceedings of the SIGCHI conference on Human Factors in computing systems*, pp. 791-800 (2006).

(Continued)

*Primary Examiner* — Marcus T Riley
(74) *Attorney, Agent, or Firm* — Hamilton, Brook, Smith & Reynolds, P.C.

(57) ABSTRACT

Presented are a system and methods for automatically extracting, analyzing and visualizing conversational turn-taking patterns during co-located and remote social interactions. The visualization tool measures group conversation dynamics based on wirelessly or otherwise obtained electronic sensor data corresponding to each participant. The group conversation dynamics that are determined (or detected) include, per participant, turn duration, turn-taking speed, number of turns, number of overlapping turns, number of successful interruptions and number of unsuccessful interruptions. Also calculated are participant mirroring statistics, activity statistics, consistency statistics, influence statistics and social network statistics. The visualizations may be output with user configurable parameters.

27 Claims, 9 Drawing Sheets

BLOCK DIAGRAM OF SPEECH DETECTION METHOD

(56) References Cited

U.S. PATENT DOCUMENTS

| | | | |
|---|---|---|---|
| 2014/0163981 A1* | 6/2014 | Cook | G10L 15/26 704/235 |
| 2014/0249891 A1 | 9/2014 | Olguin Olguin et al. | |
| 2015/0206011 A1* | 7/2015 | Jerauld | A61B 5/486 345/8 |

OTHER PUBLICATIONS

Basu, S., et al., "Towards Measuring Human Interactions in Conversational Settings," *Proceedings of the IEEE International Workshop on Cues in Communication* (2001).

Bergstrom, T. & Karahalios, K., "Conversation Clock: Visualizing audio patterns in co-located groups," *Proceedings of the Hawaii International Conference on System Sciences*, p. 78 (2007).

Curhan, J., and Pentland, A., "Thin Slices of Negotiation: Predicting Outcomes from Conversational Dynamics within the First 5 minutes," *Journal of Applied Psychology*, 92(3): 802-811 (2007).

DiMicco, J.M., et al., "Influencing group participation with a shared display," *Proceedings of the ACM Conference on Computer Supportive Cooperative Work*, pp. 614-623 (2004).

DiMicco, J.M., et al., "Research on the Use of Social Software in the Workplace," *Computer Supported Collaborative Workshop Social Networking in Organizations*, San Diego, California, Nov. 8-12, 2008.

DiMicco, J.M., et al., "The Impact of Increased Awareness while Face-to-Face," *Human-Computer Interaction*, 22(1): 47-96 (2007).

Eagle, N., and Pentland, A., "Eigenbehaviors: Identifying structure in routine," *Behavioral Ecology and Sociobiology*, 63(7): 1057-1066 (2009).

Eagle, N., and Pentland, A., "Social Serendipity: Mobilizing social software," *Pervasive Computing, IEEE*, 4(2): 28-34 (2005).

Hendrick, H.W., "Ergonomics in organizational design and management," *Ergonomics*, 34(6): 743-56 (1991).

Jayagopi, D.B., et al., "Modeling Dominance in Group Conversations Using Nonverbal Activity Cues," *Audio, Speech, and Language Processing, IEEE Transactions on*, 17(3): 501-513 (2009).

Johnston, I., et al., "Experiences from a wireless sensor network deployment in a petroleum environment," *Proceedings of the 2007 International Conference on Wireless Communications and Mobile Computing*, pp. 382-387 (2007).

Karantonis, D.M., et al., "Implementation of a Real-Time Human Movement Classifier Using a Triaxial Accelerometer for Ambulatory Monitoring," *IEEE Transactions on Information Technology in Biomedicine*, 10(1): 156-167 (2006).

Kim, T., et al., "Enhancing Organizational Communication using Sociometric Badges," *IEEE 11th International Symposium on Wearable Computing* (2007).

Kim, T., et al., "Sociometric badges: Using sensor technology to capture new forms of collaboration," *Journal of Organizational Behavior*, 33: 412-427 (2012).

Kirkman, B.L., et al., "The impact of team empowerment on virtual team performance: the moderating role of face-to-face interaction," *Academy of Management*, 47(2): 175-92 (2004).

Koyrakh, I., et al., "Identifying speech and conversations in wearable sensor networks," 2008.

Kyulk, O., et al., "Real-Time Feedback on Nonverbal Behavior to Enhance Social Dynamics in Small Group Meetings," *Proceedings of the Converence of Machine Learning for Multi-modal Ineraction*, pp. 150-161 (2005).

Mark, G., "Meeting at the desktop: an empirical study of virtually co-located teams," *Proceedings of the European Conference on Computer Supported Cooperative Work*, pp. 159-178 (1999).

Olguin-Olguin, D., "Sociometric badges: Wearable technology for measuring human behavior," *Master's Thesis, Massachusetts Institute of Technology* (2007).

Olguin-Olguin, D., et al., "Capturing Individual and Group Behavior with Wearable Sensors," *Submitted to the AAAI Spring Symposium on Human Behavior Modeling* (2009).

Olguin-Olguin, D., et al., "Sensible Organizations: Technology and Methodology for Automatically Measuring Organizational Behavior," *IEEE Transactions on Systems, Man, and Cybernetics-Part B: Cybernetics*, 39(1):,43-55 (Feb. 2009).

Olguin-Olguin, D., et al., "Sensor-based organisational design and engineering," *Int. J. Organisational Design and Engineering*, 1(1/2): 69-97 (2010).

Pedersen, E., et al., "Tivoli: An electronic whiteboard for informal workgroup meetings," *Proceedings Conference on Human Factors in Computer Systems*, pp. 391-398 (1993).

Pentland, A., "Automatic mapping and modeling of human networks," *Physica A*, 378: 59-67 (2006).

Stoltzman, W.T., "Toward social signaling framework: Activity and emphasis in speech," *Master's Thesis, Massachsetts Institute of Technology* (2006).

Streitz, A., et al., "DOLPHIN: Integrated Meeting Support Across LiveBoards, Local and remote Desktop Environments," *Proceedings of the ACM Conference on Computer Supported Cooperative Work*, pp. 345-358 (1994).

Sung, M., et al., "Wearable feedback systems for rehabilitation," *Journal of NeuroEngineering and Rehabilitation*, 2: 17-28 (Jun. 2005).

Tang, J., et al., "ConNexus to Awarenex: Extending Awareness of Mobile Users," *Proceedings of Conference on Human Factors in Computer Systems*, pp. 221-228 (2001).

Trist, E., "The evolution of socio-technical systems: a conceptual framework and an action research program," in Perspectives on Organizational Design & Behavior, Van de Ven, A.H. & Joyce, W.F. pp. 19-75 (1981).

Waber, B. N., et al., "Organizational engineering using sociometric badges," available at SSRN 1073342, (2007).

Waber, B.N., and Pentland, A., "Augmented Social Reality," *IEEE 11th International Symposium on Wearable Computing* (2007).

Waber, B.N., et al., "Understanding Organizational Behavior with Wearable Sensing Technology," *Academy of Management Annual Meeting*, Anaheim, CA (2008).

Wu, L., et al., "Mining Face-to-Face Interaction Networks using Sociometric Badges: Predicting Productivity in an IT Configuration Task," *Proceedings of the International Conference on Informational Systems* (2008).

Yankelovich, N., et al., "Improving Audio Conferencing: Are two ears better than one?," *Proceedings on the 2006 Conference on Computer Supported Cooperative Work*, pp. 333-342 (2006).

Ara, K. et al., "Predicting Flow State in Daily Work through Continuous Sensing of Motion Rhythm", IEEE Sixth International Conference on Networked Sensing Systems (INSS) (Jun. 17-19, 2009).

Notification of Transmittal of the International Search Report and The Written Opinion of the International Searching Authority mailed Feb. 6, 2015 for International Application No. PCT/US2014/038035 entitled "Social Sensing and Behavioral Analysis System".

Notification of Transmittal of the International Preliminaery Report on Patentability mailed Dec. 17, 2015, for International Application No. PCT/US2014/038035 entitled "Social Sensing and Behavioral Analysis System".

* cited by examiner

BLOCK DIAGRAM OF SPEECH DETECTION METHOD

BLOCK DIAGRAM OF TURN-TAKING DETECTION METHOD.

BLOCK DIAGRAM OF CONVERSATION DETECTION METHOD.

MEETING EFFECTIVENESS VISUALIZATION.

PARTICIPANT'S TURN-TAKING GRAPH.

PARTICIPATION CHART.

METHODS FOR AUTOMATICALLY ANALYZING CONVERSATIONAL TURN-TAKING PATTERNS

RELATED APPLICATIONS

This application claims the benefit of U.S. Provisional Application No. 61/764,911 filed Feb. 14, 2013. The entire teachings of the above application are incorporated herein by reference.

BACKGROUND OF THE INVENTION

This invention relates to the field of speech processing, and more specifically to the automatic analysis of conversations in unconstrained environments.

Social interactions can be captured using electronic sensors and analyzed by applying audio, speech, and language processing, visual processing, multimodal processing, as well as other human-computer interaction and ubiquitous computing techniques. As described by Gatica-Perez (2009): "the computational analysis of group conversations has an enormous value on its own for several social sciences and could open doors to a number of relevant applications that support interaction and communication, including self-assessment, training and educational tools, and systems to support group collaboration through the automatic sensing, analysis, and interpretation of social behavior". See Gatica-Perez, D. "Automatic nonverbal analysis of social interaction in small groups: A review". Image and Vision Computing, Vol. 27, No. 12, pp. 1775-1787, November 2009.

Olguin-Olguin (2007) discloses the use of wearable "sociometric badges" capable of automatically measuring the amount of face-to-face interaction, conversational time, physical proximity to other people, and physical activity levels using social signals derived from vocal features, body motion, and relative location to capture individual and collective patterns of behavior. The percentage of time when an individual was engaged in a conversation was measured. However, the author does not contemplate or teach other methods for the automatic analysis of conversation dynamics such as turn-taking patterns using data captured by such wearable sensors. See Olguin Olguin, D. "Sociometric badges: wearable technology for measuring human behavior". Thesis (S. M.)—Massachusetts Institute of Technology, School of Architecture and Planning, Program in Media Arts and Sciences, 2007.

Kim et al. (2008) present a "meeting mediator" system also based on the sociometric badges to detect social interactions and provide feedback on mobile phones in order to enhance group collaboration. Variables used by this system include: speaking time, average speech segment length, variation in speech energy and variation in body movement. The phone visualization was limited to four participants and designed for certain types of collaborations for which balanced participation and high interactivity is desirable. Each of the four participants was represented as colored squares in the corners of the screen. The color of a central circle gradually changed between white and green to encourage interactivity, with green corresponding to a higher interactivity level. Balance in participation was displayed through the location of the circle: the analogy is such that the more a participant talks, the stronger they are pulling the circle closer to their corner. They also displayed each member's speaking time by varying the thickness of the lines connecting the central circle with each member's corner. The visualization was updated every 5 seconds. See Kim, T., Chang, A., Holland, L., and Pentland, A. "Meeting mediator: enhancing group collaboration using sociometric feedback". In Proceedings of the ACM conference on computer supported cooperative work, pp. 457-466, 2008.

Jayagopi et al. (2009) used the following features to model dominance in group conversations that were recorded using video and a circular microphone array: total speaking energy, total speaking length, total speaker turns, speaker turn duration histogram, total successful interruptions, and total speaker turns without short utterances. However participants were asked to wear both a headset and a lapel omnidirectional microphone and were constrained to a meeting room. Three cameras were mounted on the sides and back of the room. See Jayagopi, D. B., et al "Modelling Dominance in Group Conversations Using Nonverbal Activity Cues," IEEE Transactions on Audio, Speech and Language Processing, Vol. 17, No. 3, pp. 501-513, March 2009.

Salamin and Vinciarelli (2012) propose an approach for the automatic recognition of roles in conversational broadcast data, in particular news and talk-shows. The approach makes use of behavioral evidence extracted from speaker turns to infer the roles played by different individuals. Their approach consists of (1) extracting the turns using a "speaker diarization" approach that gives a list of triples:

$$S=\{(s_1, t_1, \Delta t_1), \ldots, (s_N, t_N, \Delta t_N)\}$$

where N is the number of turns extracted by the diarization approach, $s_i \in A=\{a_1, \ldots a_G\}$ is a speaker label, G is the total number of speakers detected during the diarization, $t_i$ is the starting time of turn i, and $\Delta t_i$ is its length.

The turn sequence S provides information about who speaks when and for how long. This makes it possible to extract features accounting for the overall organization of turns as well as for the prosodic behavior of each speaker. The second step in their approach consists of (2) extracting different features that account for the way an individual participant contributes to the turn organization (total number of turns for current speaker, time from the beginning of recording to first turn of current speaker, average time between two turns of current speaker) as well as features that account for how a particular turn contributes to the overall turn organization (turn duration, time after last turn of the current speaker, among others). After the feature extraction step, the sequence S of turns is converted into a sequence $X=\{x_1, \ldots, x_N\}$ of observations, where the components of vectors $x_i$ correspond to some of the features described previously. See Salamin, H., and Vinciarelli, A. "Automatic Role Recognition in Multiparty Conversations: an Approach Based on Turn Organization, Prosody and Conditional Random Fields". IEEE Transactions on Multimedia, Vol. 14, No. 2, pp. 338-345, April 2012.

Kim et al. (2012) describe a set of features used to study turn-taking patterns:

1) Turn duration statistics. Mean, median, maximum, variance and minimum of speaker turns duration in the clip as well as the average number of turns.

2) Turn-taking count across speakers. This information can be modeled with bigram counts, i.e. the number of times participants from different groups take turns one after each other.

3) Amount of overlap relative to the clip duration.

4) Turn keeping/turn stealing ratio in the clip. The ratio between the number of times a speaker change happens and the number of times a speaker change does not happen after an overlap. See Kim, S., Valente, F., and Vinciarelli, A. "Automatic detection of conflicts in spoken conversations: ratings and analysis of broadcasting political debates". Proceedings of IEEE International Conference on Audio, Speech and Signal Processing, 2012.

Dong et al. (2012) describe an approach based on Markov jump processes, to model group interaction dynamics and group performance. They estimate conversational events such as turn taking, backchannels, turn-transitions and link the micro-level behavior with macro-level group performance. The authors define a speaking turn as one continuous segment of fixed length (e.g. not less than 1.5 s) where a participant starts and ends her/his speech. They model the following aspects of the turn-taking structure: (i) taking the turn: if nobody is speaking and somebody takes the turn; (ii) backchannel: a situation where a subject Y speaks after a subject X for less than 1 s. (e.g. "yes" or "uh-huh"); (iii) speaker transitions: if somebody is ending a turn and another person takes the turn; (iv) turn competition: a situation in which two subjects are speaking at the same time and one ends before the other. See Dong, W., Lepri, B., Kim, T., Pianesi, F., and Pentland, A. "Modeling Conversational Dynamics and Performance in a Social Dilemma Task". 5th International Symposium on Communications Control and Signal Processing (ISCCSP), 2012.

U.S. Pat. No. 6,246,986 discloses an interactive voice response unit (VRU) that controls at least one prompt delivered by such unit, including a recognizer that discards input signals that fail to meet usefulness criteria and a phrase detector (claim 1). It also discloses a VRU where the phrase detector includes a turn-taking module that ascertains the rate at which the phrase detector detects significant signal segments (claim 18), the lengths of silences between significant signal segments (claim 19), inflections at which it detects significant signal segments (claim 20).

U.S. Pat. No. 8,126,705 describes a system and methods for automatically adjusting floor controls for a conversation. A method of identifying a conversation includes the steps of extracting streams of feature data from a conversation and analyzing them in various combinations of users to identify a conversation between two or more users. Another method receives one or more audio streams, distinguishes one or more audio sub-streams, mixes the sub-streams, analyzes one or more conversational characteristics of two or more users and automatically adjusts the floor controls.

U.S. Pat. No. 8,131,551 discloses a system and method for controlling the movement of a virtual agent while the agent is speaking with a human. The method receives speech data to be spoken by the virtual agent, performs a prosodic analysis of the speech data, selects matching prosody patterns from a speaking database, and controls the virtual agent movement according to selected prosody patterns.

Prior systems and methods assume that the number of participants in the conversation is fixed and known a priori, that all participants in the conversation are co-located, and that the turn characteristics are pre-defined (e.g., the length of a turn or the length of a pause between turns).

SUMMARY OF THE INVENTION

The above-mentioned prior art deficiencies are overcome by our method by automatically detecting the number of participants in a conversation that can take place in the same location or in distributed settings (e.g. by combining wearable sensor data with phone, mobile phone, or video conference systems), detecting when each participant is speaking, and the start and end time of each speaking turn for all speakers. Other improvements are achieved by (1) filtering out audio segments in which no speech or interaction data is detected, and by (2) allowing users of our analysis software to configure different parameters (e.g. minimum and maximum turn length, minimum and maximum pause length between speaking turns, short utterance length, among others) before carrying out the turn-taking analysis.

By using mobile portable devices such as mobile phones, electronic ID badges, and video conferencing systems we can automatically track when two or more participants join or leave a conversation, automatically adjust our speech detection and conversation analysis algorithms, analyze each conversation separately, and visualize in real time the conversation dynamics. Conversation patterns that we are capable of analyzing include: the overall turn-taking statistics and turn-taking matrix; individual participant's speech activity, consistency, participation, and dominance levels; and pair wise mirroring and influence metrics across participants in a conversation.

Our methods and system have been reduced to practice by combining "Sociometric Badges" (Olguin Olguin, 2007 incorporated herein by reference), wearable electronic ID badges capable of detecting when two or more people are directly facing each other (using an infrared sensor) or are in close proximity to each other (using Bluetooth signal scanning for example), and several speech processing and conversation analysis algorithms. We combine the face-to-face infrared sensor detections and Bluetooth proximity data (radio signal strength measurement) with speech detection algorithms in order to detect in real time when a group of people are having a conversation, when and for how long each participant is speaking, automatically analyze turn-taking patterns and speech features during each conversation, and visualize the conversation dynamics. Data collected by the sociometric badges can be transferred in real time via Bluetooth (for example) and combined with audio streams from remote participants interacting via phone or video conferencing.

We describe a real-time meeting visualization application that provides feedback to participants in a conversation and displays information such as: dominance (percentage of total speaking time by each participant), number of turns across participants, and overall meeting effectiveness.

Preferred embodiments measure various dynamics (attributes and characteristics) of a group of people in conversation. To measure these group conversation dynamics, embodiments determine existence of a conversation between at least two people and determine turn-taking among the participants in the conversation. In particular, an embodiment (computer method or system), from a stream of speech audio data corresponding to the conversation, identifies participants' portions of the speech audio data as speech or silence. As a function of the identified speech and silence of participants in the conversation, the invention method and system detect turn-taking among the participants and output indications of participants' turns taken in the conversation.

The method detecting turn-taking includes determining per participant: turn duration, number of turns, turn-taking speed (e.g., numbers of turns per minute or other unit of time) and number of overlapping turns. The method preferably includes determining number of successful and unsuccessful interruptions. In other embodiments, the detection method further determines per participant:
number of turns taken before this participant,
number of turns taken after this participant,
number of self turns taken by this participant,
number of speaking segments,
number of pauses,
average speaking segment length, and/or
average pause length.

In embodiments, from the sensor data the method and system collect body movement (including body posture) data corresponding to the participants. Based on the collected body movement (and body posture) data and the identified speech and silence, the method/system calculates four social signals, namely mirroring, activity, consistency and/or influence statistics of a participant. Likewise from the sensor data, embodiments collect speech feature data (e.g. volume and fundamental frequency) corresponding to participants, and calculate these social signaling statistics of a participant with respect to speech features. The method/system may collect data on any one or combination of centrality, closeness, degree of centrality and cohesion. Based on this collected data and the identified speech and silence, the method/system can calculate social network statistics of the participant. Some embodiments calculate the social network statistics (features) on a corresponding turn-taking matrix of the participant.

Embodiments provide a variety of output display screens having graphical and other indicia illustrating any combination of:
different participants in the conversation,
current participant speaking,
number of turns each participant has taken,
dominance of a participant,
turn duration of a given participant,
number of turns taken by the given or a certain participant,
number of turns taken before the given or certain participant,
number of turns taken after the given or certain participant,
number of self-turns taken by a participant (given or certain participant),
turn-taking speed of a participant,
number of overlapping turns,
number of successful interruptions,
number of unsuccessful interruptions,
social signaling statistics of participants, and/or
participation balance of participants.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 5 illustrates separately a participant's turn-taking graph. FIG. 6 illustrates separately a participation chart. FIG. 7 illustrates separately a meeting-effectiveness graph.

DETAILED DESCRIPTION OF THE INVENTION

A description of example embodiments of the invention follows.

The teachings of all patents, published applications and references cited herein are incorporated by reference in their entirety.

Figure 8:
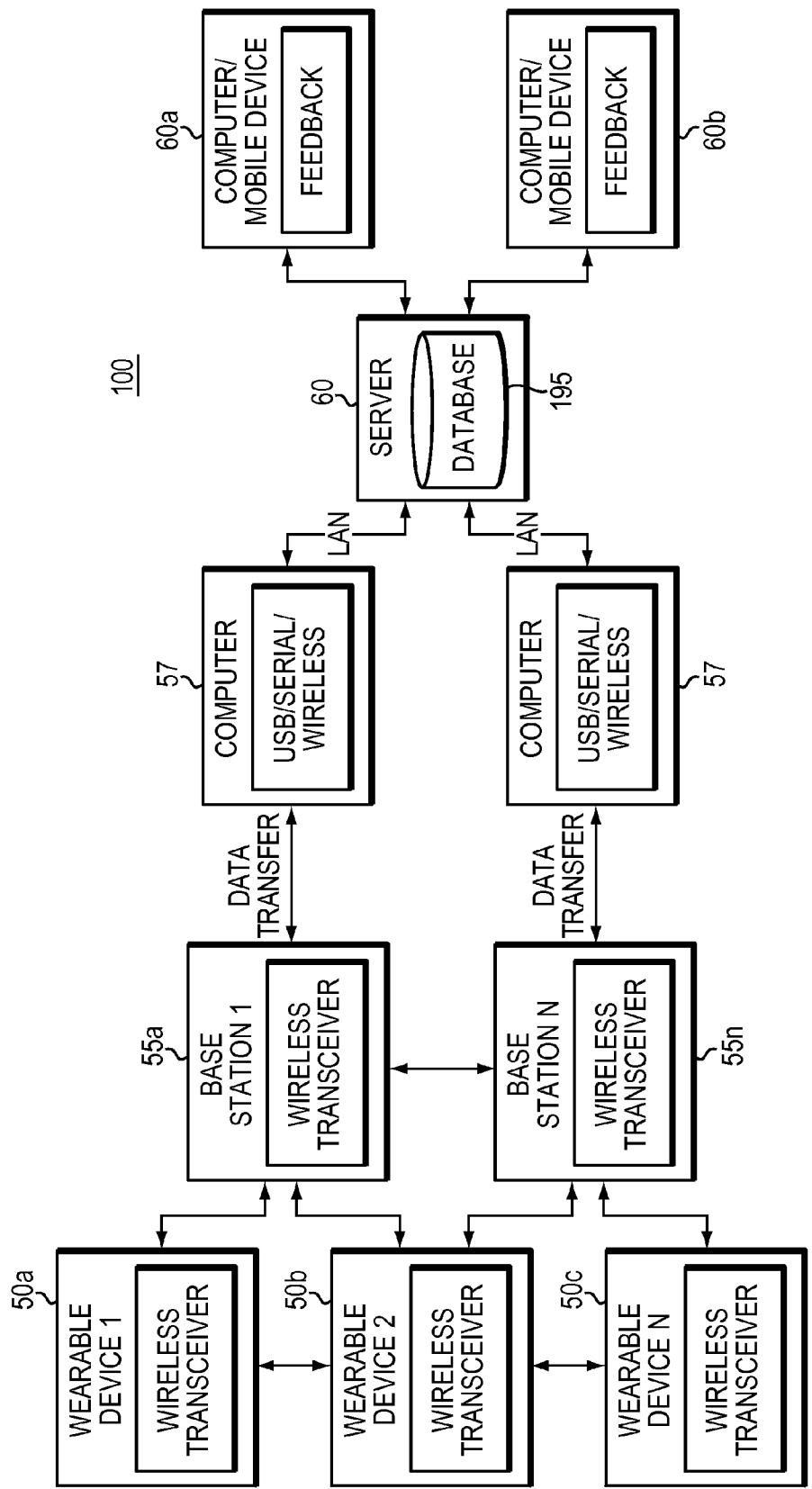
FIG. 8 is a block diagram of a sensor-based system embodying the present invention.

The proposed as shown in FIG. 8 is comprised of one or more wearable sensing and data capturing devices 50 $a \ldots n$ (generally 50) functioning in a wireless sensor network, one or more radio base stations 55 $a \ldots n$, a computer system 57 with server 60, and several data processing routines (modules) discussed in FIGS. 1-4.

People (e.g., employees) carry or wear wearable sensors/data capturing devices 50, the devices 50 measure human behavior (social interaction, activities, location, relative orientation, etc.). These devices 50 can be mobile devices such as cell phones, PDAs, or electronic badges that collect data and communicate with a database 195 (via Ethernet or wirelessly) to store and retrieve information.

The database 195 stores all the information collected by the wearable sensors/devices 50. In particular, the database 195 stores individual attributes (values, attitudes, self-concept, abilities, personality, job satisfaction, etc.); sociometric data captured from sensors 50 (speaking state, speaking style, motion state, location, face to face "f2f" interaction, proximity, etc.); group attributes (team assignment, communication frequency, social network features derived from the sociometric data); and performance data (projects or tasks, completion time, success/failure, resources, follow-ups, etc.) from each person in an organization in order to manage the vast amounts of information generated by the system 100. Database software includes: MySQL, Microsoft SQL Server, Oracle, and IBM DB2. Analysis software includes: Matlab, Microsoft Visual Studio, UCINET, among others.

In addition to the wearable sensors 50, base stations 55 can be placed in fixed locations inside a building in order to track the location of interaction events as well as subjects. A central computer system 57, 60 can be used for data collection. Data from the wearable sensors 50 is transferred wirelessly to the base stations 55 and then from base stations 55 to computer 57. From computers 57, the data is uploaded to a server 60. The base stations 55 may contain environmental sensors (temperature, light, sound, movement, activity, etc.) that capture the current conditions in an office environment, such as the number of people walking by, ambient noise, temperature and lighting conditions.

As mentioned above, the wearable sensing devices 50 may include: electronic badges, mobile phones, wrist-mounted devices, head-mounted devices, and electronic textiles, among others. These wearable devices 50 function as self-contained monitoring devices and communicate with each other and with the fixed radio base stations 55 in a wireless sensor network. The wearable sensing devices 50 preferably have a small form factor, are comfortable to wear over long periods of time, and have a long battery life. And device 50 has a user input interface 45.

Figure 9:
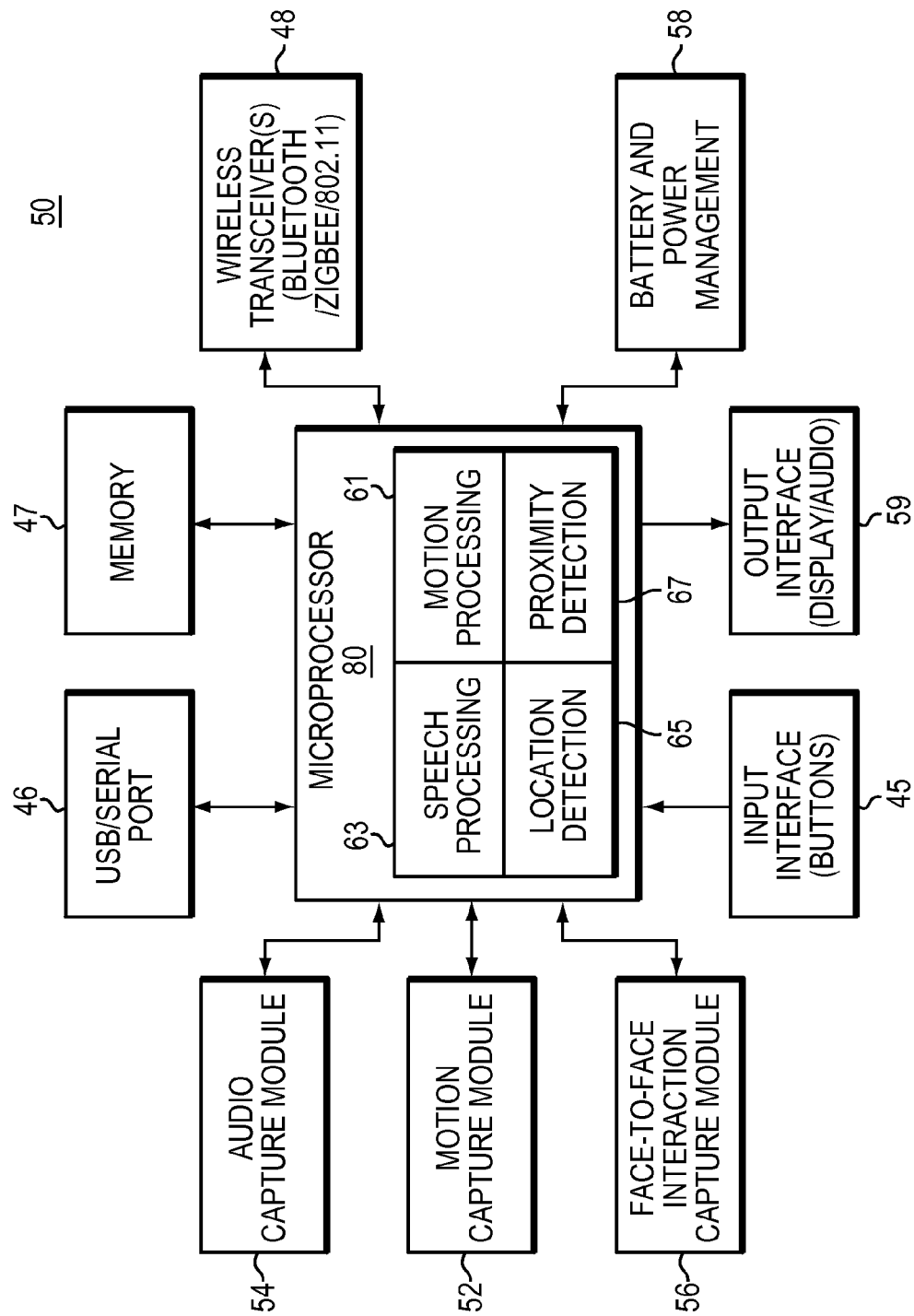
FIG. 9 is a block diagram of wearable data capturing devices and sensors employed in the system of FIG. 8.

FIG. 9 shows the block diagram of an exemplary wearable device 50. Preferably devices 50:
a) have motion processing 61 that recognizes common daily human activities (such as sitting, walking and running, and various body postures) in real time using accelerometers (motion capture module) 52
b) have speech processing 63 that extracts speech features (e.g. volume and fundamental frequency) in real time to capture non-linguistic social signals such as interest and excitement, and unconscious back-and-forth interjections, while ignoring the words in order to assuage privacy concerns c) communicate with base stations 55 over radio 48 to transfer data and communicate with each other 50 to measure the radio signal strength (and hence estimate proximity 67 and location 65)

d) perform indoor user localization 65 by measuring received signal strength and implementing triangulation algorithms; and e) capture face to face interactions using IR sensors in module 56 along with location and proximity detection 65, 67.

In one embodiment, each sensing device 50 uses an omnidirectional microelectromechanical systems (MEMS) microphone (Knowles Acoustics, SPM0103-NE3) 54 to capture the user's speech and extract different speech features without recording the actual speech signal by speech processing 63. Preferably, the microphone at 54 is connected to a noninverting operational amplifier (Analog Devices, AD8542), with a high-pass filtering cutoff frequency of 85 Hz and a low-pass cutoff frequency of 4000 Hz. The amplified microphone signal is then applied to an array of micropower single-op-amp Sallen-Key bandpass filters that divide the speech frequency spectrum into four octaves: f1 from 85 to 222 Hz, f2 from 222 to 583 Hz, f3 from 583 to 1527 Hz, and f4 from 1527 to 4000 Hz. A diodecapacitor peak detector is used after each bandpass filter to obtain the spectral envelope in each frequency band. These four spectral envelopes are used to segment the audio signal into speaking and nonspeaking regions.

A three-axis MEMS accelerometer (such as Analog Devices, ADXL330) 52 is used to detect when a person is moving and to identify (via motion processing 61) different activities and/or body postures such as sitting, standing, walking, or running. An IR transceiver module (such as Vishay, TFDU4300) 56 is used to detect when two people are facing each other. A bridged-output audio power amplifier (such as Analog Devices, SSM2211) drives an electromagnetic speaker at 59 on the device 50 to play back messages and reminders.

The main processing unit 80 is an ARM microcontroller (Atmel, AT91SAM7S256) for example. A 2.4-GHz wireless transceiver (Chipcon, CC2500) and a class 2.0 Bluetooth module (BlueRadios, BR-46AR) 48 have been incorporated for enabling wireless communications with fixed base stations 55 and other Bluetooth-enabled devices 50. A microSD memory card socket 47 has been included for storing data when the user is out of range of a fixed point or when the device 50 is used as a selfcontained sensor package. The device 50 is powered by a 950-mAh lithium-polymer battery 58 that is rechargeable through USB 46. In addition, data can also be transferred through the USB port 46. The dimensions of the device 50 inside a plastic enclosure (housing) are 4.5×10×2 cm, and the total weight including the battery 58 is about 110 g.

Further device details may be found in "Sensible Organizations: Technology and Methodology for Automatically Measuring Organizational Behavior", D. Olguin Olguin, IEEE Transactions on Systems, Man and Cypernetics-Part B: Cypernetics, 39:1, February 2009 and "Sensor-based organizational design and engineering" D. Olguin Olguin, Int. J. Organisational Design and Engineering, Vol. 1, Nos. 1/2, 2010.

Server 60 may in turn perform the following calculations based on data and information collected and transferred by sensor devices 50.

Figure 3:
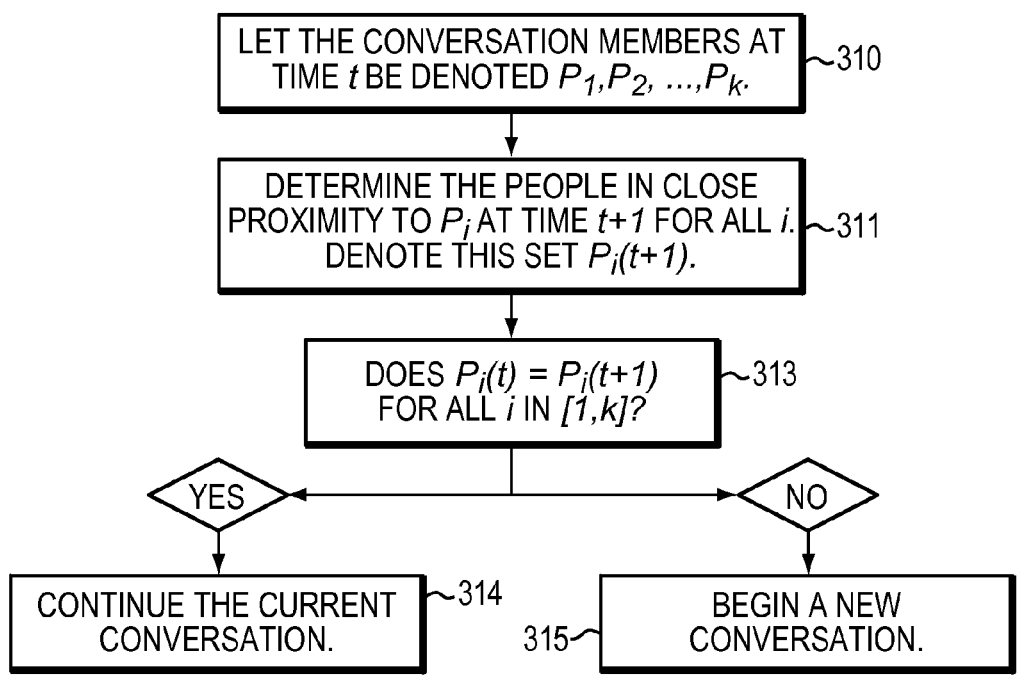
FIG. 3 is a block or flow diagram illustrating a conversation detection method of the present invention.
Figure 4:
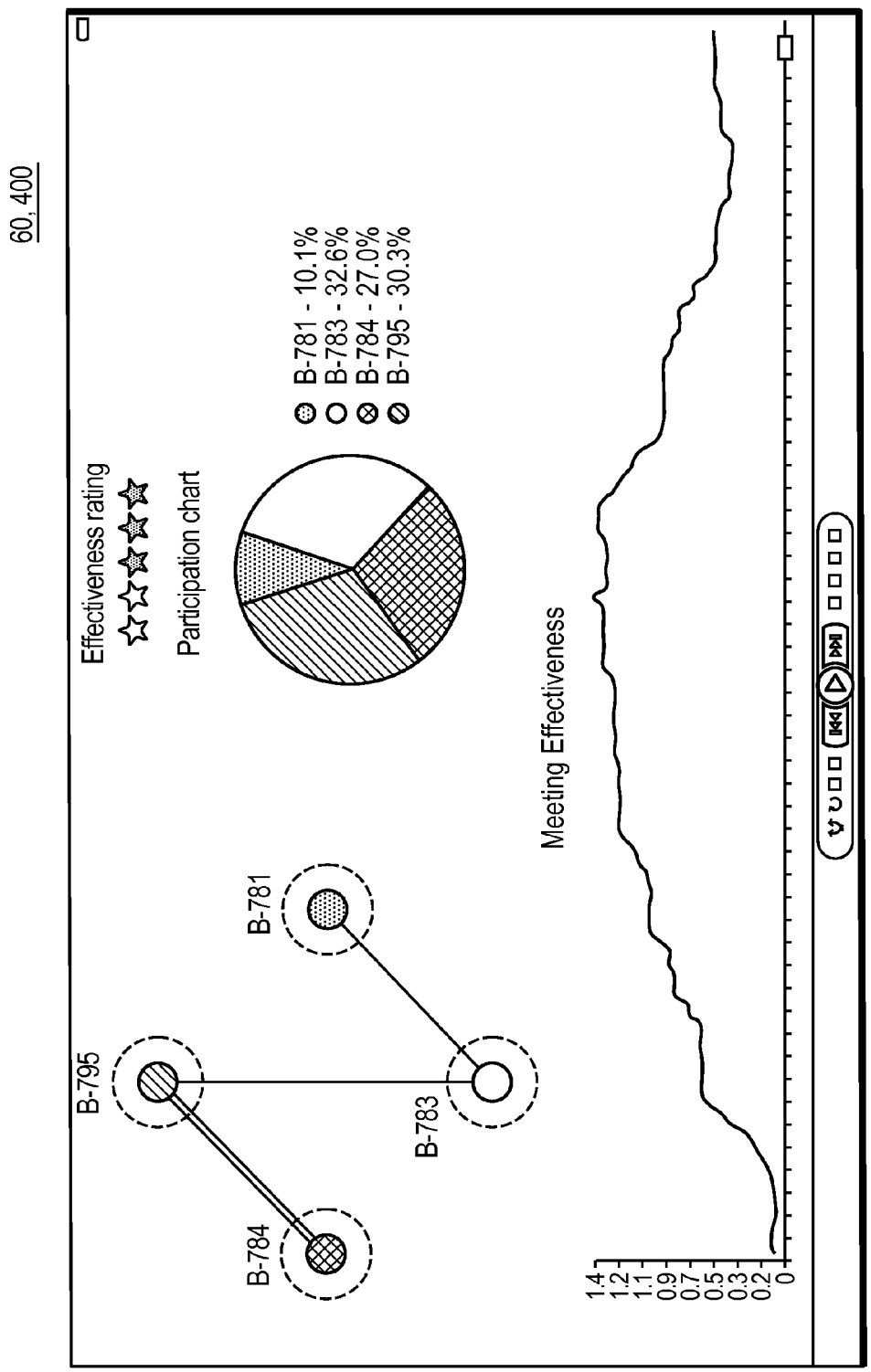
FIGS. 4-7 are schematic views of meeting dynamics and meeting effectiveness visualizations in one embodiment.
Figure 5:
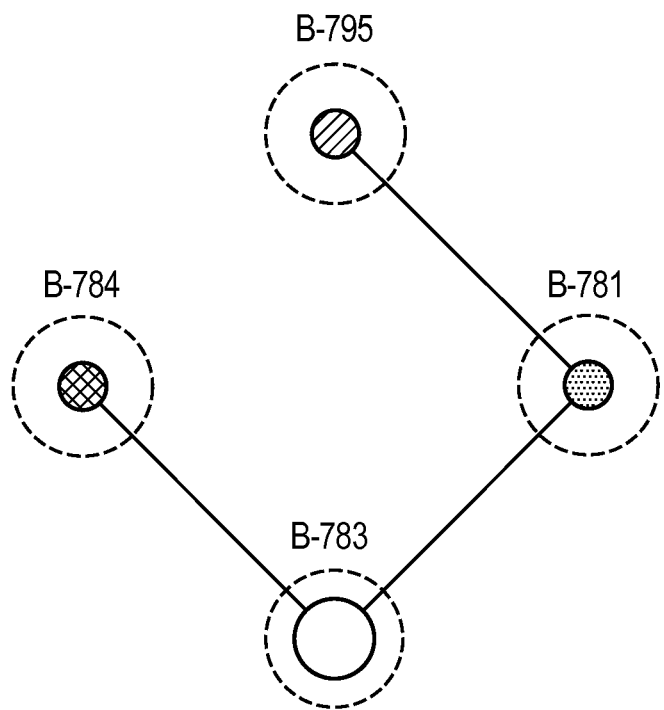
Figure 6:
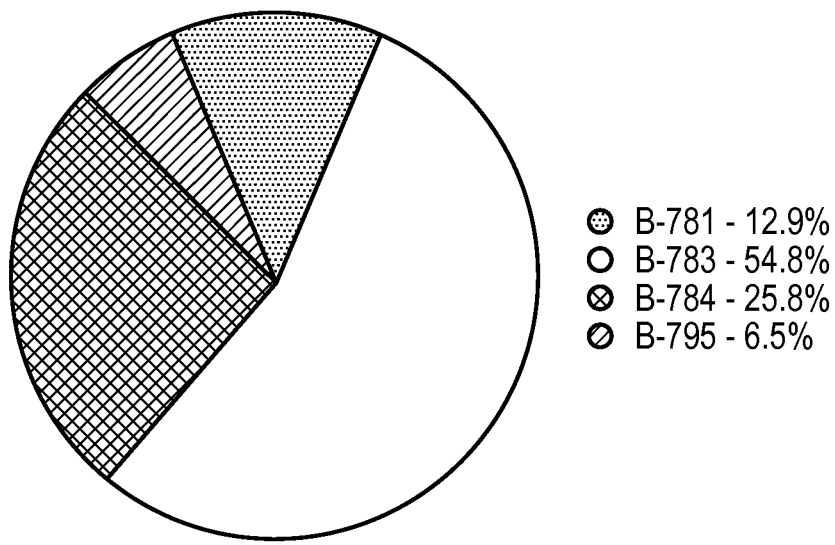

1) Conversation Detection Algorithm 300 (FIG. 3)

Sociometric badges (wearable devices 50) broadcast their unique ID through the infrared sensor at 56 and detect each other when they are within the infrared detection range (i.e. within one meter and within a 30-degree angle with each other). They also perform Bluetooth scanning at a predefined rate and can detect other badges/devices 50 in close proximity. The total face-to-face interaction time can be estimated by measuring the expected detection rate within controlled conditions (i.e. by increasing the distance and orientation between two IR broadcasting sensors) and assigning each infrared detection a time equal to the difference between the maximum possible number of detections in a time window of fixed length and the typical detection rate within the same time window. For example, suppose two badges/devices 50 broadcast their unique IDs every second. Further, badges/devices 50 detect each other when they are within 1-meter and 30-degrees of each other. The measured detection rate for badges/devices 50 satisfying these conditions is 75% for a period of 60 seconds. Thus, each unique ID detection describes the two badges/devices 50 being in front of each other for at least 60*(1−0.75)=15 seconds. Therefore, we quantify each infrared detection as 15 seconds of face-to-face interaction time unless there is another detection within the same 15-second interval: in this case we just extend the first detection by 15-seconds from the second detection.

We follow a similar approach in order to quantify (say by server 60) the amount of time that two or more people wearing sociometric badges 50 are in close proximity to each other. See steps 310, 311 in FIG. 3. Here, we calculate the typical detection rate of Bluetooth detections with a predefined radio signal strength and within a predefined distance.

A list of conversations can be obtained by labeling every time a person joins or leaves a conversation on a second-by-second basis (at steps 313, 314, 315 of FIG. 3). We consider any infrared detection extended by 15 seconds or any Bluetooth detection with radio signal strength greater than a known threshold, extended by 60 seconds from either badge i to badge j or from badge j to badge i:

| Timestamp | Badge 1 | Badge 2 | Badge 3 | Badge 4 |
|---|---|---|---|---|
| $t_1$ | 1 | 1 | 0 | 0 |
| $t_2$ | 1 | 1 | 0 | 0 |
| $t_3$ | 1 | 1 | 0 | 0 |
| $t_4$ | 2 | 0 | 2 | 2 |
| $t_5$ | 9 | 0 | 2 | 2 |
| $t_6$ | 2 | 0 | 2 | 2 |
| $t_7$ | 0 | 3 | 3 | 0 |
| $t_8$ | 0 | 3 | 3 | 0 |

This list can be interpreted as badges 1 and 2 starting a conversation at time $t_1$ (conversation 1), then badge 2 leaving the conversation and badges 3 and 4 joining a new conversation with badge 1 (conversation 2) at time $t_4$. Badges 2 and 3 then engage in conversation 3 from $t_6$ to $t_8$. Badges not taking part in a conversation are labeled as "0". FIG. 3 is illustrative of this conversation detection 300 processing of the present invention.

From this list the start and end times for every conversation that takes place can be retrieved, as well as the list of participants involved in each conversation. Our turn-taking analysis 200 (FIG. 2) and speech algorithms/process 110 (FIG. 1) can then run in real time for each conversation.

2) Speech Detection Algorithm

Figure 1:
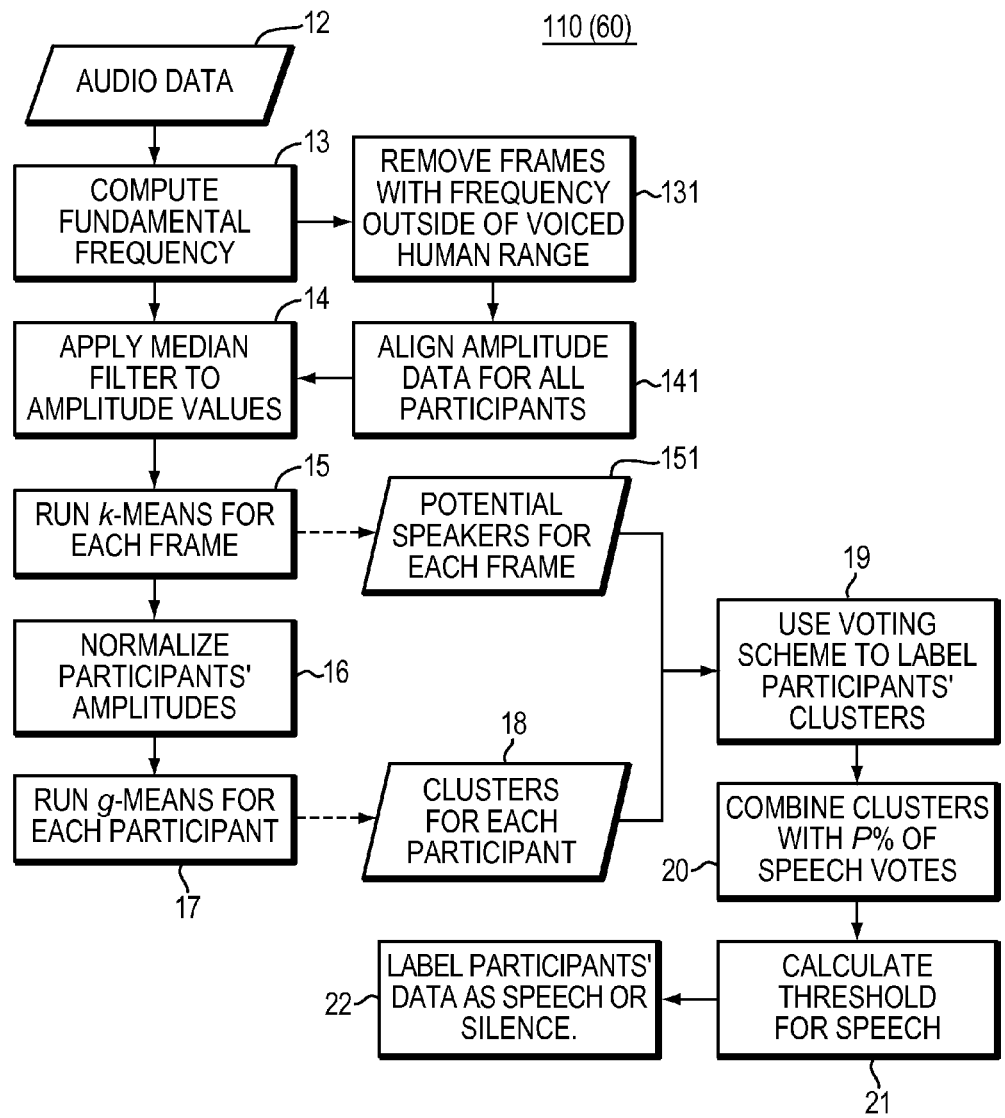
FIG. 1 is a block or flow diagram illustrating a speech detection method of the present invention.

Our speech detection algorithm 110 is outlined in FIG. 1. The speech detection process 110 is based on the unsupervised k-means algorithm applied to a stream of speech audio data 12 sampled at 8 kHz and averaged over a user-defined frame. We compute the audio average energy frame-by-frame as:

$$x = \sqrt{\frac{\sum_{i=0}^{n}(v_i - |\bar{v}|)^2}{n}},$$

v is the sample value, n is the frame length.

The frame length can be specified by the user and it typically ranges from 0.032 to 1 second.

Process step 13 (in FIG. 1) then computes the fundamental frequency ($f_0$) estimate frame-by-frame by following these steps:

1. Remove DC bias from the sample data for a full frame
2. Apply forward Fourier transformation
3. Calculate absolute magnitude of each Fourier coefficient
4. Take natural logarithm of each absolute magnitude
5. Apply inverse Fourier transformation on the vector from step 4
6. Calculate absolute magnitude for each item in result of step 5
7. Find the n highest local maximums of step 6

Process step 131 filters out audio frames with $f_0$ estimate outside the human speech fundamental frequency range (85 to 255 Hz).

An optional step 14 (in FIG. 1) consists of applying a median filter of variable length (which is a multiple of frame length) in order to smooth the amplitude data and reduces the amount of silence that will be allowed between each segment labeled as "speech."

First, the amplitude data for N audio streams are aligned in time (at 141) creating a matrix A of dimension F×N, where F is the total number of frames and N is the total number of audio streams.

Process step 15 in FIG. 1 applies the k-means algorithm with k=2 frame-by-frame to matrix A to cluster audio streams into two groups: one with low volume and one with high volume. We then limit (at process part 151) the number of potential simultaneous speakers to m (where m>0) by choosing the m streams with the highest amplitudes from the cluster with high volume. We will call this step "frame-by-frame-k-means".

All audio frames are then normalized (process step 16) by subtracting the mean of all audio amplitude frames in the audio data stream, and dividing them by the standard deviation of the audio amplitude frames:

$$X = A - \text{mean}(A)/\text{std}(A)$$

The next process part 17 consists of applying an adaptive version of the k-means algorithm, referred to as "g-means" (Hamerly and Elkan, 2003) to automatically find the best number of clusters across all audio frames for each audio stream (columns in matrix A). See Hamerly, G., and Elkan, C. "Learning the k in k-means". Proceedings of the 7th Annual Conference on Neural Information Processing Systems, 2003.

The g-means algorithm starts with a small number of k-means clusters and increases the number of clusters 18 with each iteration. The algorithm accomplishes this by splitting into two those clusters with data which does not appear to come from a Gaussian distribution. In this manner, k-means is run on the entire dataset and all clusters to refine the current solution.

G-means at process part 17 repeatedly makes decisions based on a statistical test for the data assigned to each cluster. If the data currently assigned to a k-means cluster appear to be Gaussian, then that data is represented with only one center. However, if the same data do not appear to be Gaussian, multiple clusters are used to model the data properly.

In order to detect whether the data assigned to a cluster are sampled from a Gaussian, two alternative hypotheses are defined:

H0: The data in the cluster are sampled from a Gaussian distribution.

H1: The data in the cluster are not sampled from a Gaussian distribution.

If we fail to reject the null hypothesis $H_0$, then one cluster is sufficient to model its data, and we should not split the cluster into two sub-clusters. If we reject $H_0$, then we should further split the cluster. The statistical test proposed by Hamerly and Elkan (2003) is based on the Anderson-Darling statistic:

$$A^2(Z) = -\frac{1}{n}\sum_{i=1}^{n}(2i-1)[\log(z_i) + \log(1 - z_{n+1-i})] - n$$

For the case where $\mu$ and $\sigma$ are estimated from the data, we must correct the statistic according to:

$$A_*^2(Z) = A^2(Z)\left(1 + \frac{4}{n} - \frac{25}{n^2}\right)$$

Given a subset of data X in d dimensions that belongs to center c, the hypothesis test proceeds as follows:

1) Choose a significance level $\alpha$ for the test.
2) Initialize two clusters as the "children" of c.
3) Run k-means on these two clusters in X. Let $c_1$ and $c_2$ be the child clusters chosen by k-means.
4) Let $v = c_1 - c_2$ be a d-dimensional vector that connects the two clusters, then project X onto v:

$$x_i' = \frac{\langle x_i, v \rangle}{\|v\|^2}$$

X' is a one-dimensional representation of the data projected onto v. Transform X' so that it has mean 0 and variance 1.

5) Let $z_i = F(x_i')$. If $A^{*2}$ (Z) is in the range of non-critical values at confidence level $\alpha$, then fail to reject $H_0$, keep the original center, and discard $\{c_1, c_2\}$. Otherwise, reject $H_0$ and keep $\{c_1, c_2\}$ in place of the original center.

The final step 19 is a voting scheme that combines the results from the "frame-by-frame-k-means" step (at 151) and the "g-means" steps 17 and 18 and selects which clusters should be grouped and labeled as "speech":

i) If there is at least one cluster with more than P % of the frames labeled as containing a "potential speaker" (resulting from the "frame-by-frame-k-means" step 151) and there are more than 2 clusters:

a) Group clusters (at 20) with more than P % speech labels.
b) Set speech threshold 21 as the minimum amplitude in the sorted normalized amplitude array containing all amplitudes in that group of clusters.
c) Label 22 as "speech" each frame with amplitude greater than the threshold 21 and where the audio stream was labeled as a "potential speaker" by the frame-by-frame-k-means step 151.

ii) If there are no clusters with more than P % of the frames labeled as speech (resulting from the "speaker-k-means" step 15, 151):
Label all frames as silence 3) Turn-Taking Detection Algorithm 200 (FIG. 2)

Figure 2:
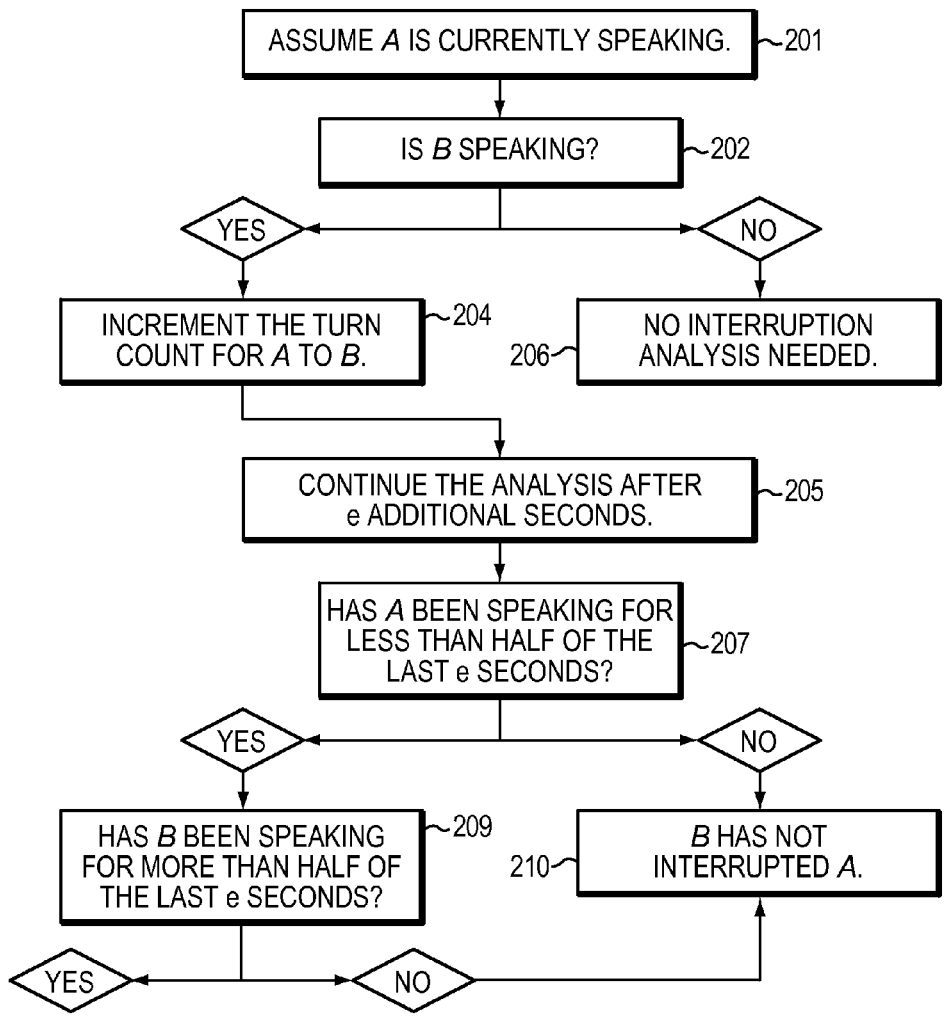
FIG. 2 is a block or flow diagram illustrating a turn-taking detection method of the present invention.

Our turn-taking algorithm (process 200 by server 60) in FIG. 2 is based on the results from the speech detection algorithm (process 110) described above in FIG. 1. A turn between A and B occurs if B starts speaking within a time interval w after A.

Turn-taking detection 200 is outlined in FIG. 2 and computed as follows:
1. Let $S(A, t)=1$ if X is speaking at time frame t (step 201)
2. Let $I(A, B, t)=1$ if X and Y detect each other at time frame t (step 202)
3. A turn between A and B will occur at time t if
   a. $I(A, B, t')=1$ for all t' between t−w and t, and
   b. $S(A, t')=1$ for all t' between t−w and t−q for some $q \geq 0$ and
   c. $S(B, t)=1$ See steps 204, 206 in FIG. 2.

A turn between A and B at time frame t will be counted as successful interruption if $$1. \sum_{t'=t}^{t'=t+e} S(X, t') < \frac{e}{2}$$ (step 207)

$$2. \sum_{t'=t}^{t'=t+e} S(Y, t') > \frac{e}{2}$$ (step 209)

where e is the interruption window length. Otherwise, the interruption between A and B is considered to be unsuccessful at 210 (FIG. 2).

Embodiments employ the foregoing turn-taking detection 200 and determine per participant:
turn duration,
number of turns,
turn-taking speed (e.g., number of turns per unit of time),
number of overlapping turns,
number of turns taken before this participant,
number of turns taken after this participant,
number of self-turns taken by this participant,
number of speaking segments,
number of pauses,
average speaking segment length, and/or
average pause length.

4) Conversation Dynamics Features

This is a list of functions that server 60 may apply to different speech and body movement sensor data 61, 63, where the word "FUNCTION" can be replaced by: sum, mean, median, maximum, minimum, variance, entropy, percentage.

Turn duration statistics include: FUNCTION(turn duration) calculated during time interval T for each interaction participant.

Turn-taking statistics (matrix) include: FUNCTION(number of turns) calculated during time interval T across interaction participants, e.g. speaker B(rows) after speaker A(columns). Turn-taking speed of a participant is then calculated as number of turns taken by that participant per unit of time.

Entry (A,B) corresponds to the number of times B's turn follows a turn taken by A. Statistics for turns taken after participant A (vector) include: FUNCTION(number of turns after A) calculated during time interval T across interaction participants, i.e. the row in the turn-taking matrix corresponding to participant A.

Statistics for turns taken before participant A (vector) include: FUNCTION(number of turns before A) calculated during time interval T across interaction participants, i.e. the column in the turn-taking matrix corresponding to participant A.

Statistics for self-turns (scalar) include: FUNCTION(number of self-turns) calculated during the time interval T, i.e. the row and column corresponding to participant A.

Overlap statistics (matrix) include: FUNCTION(number of overlapping turns) calculated during time interval T across interaction participants, e.g. speaker A and speaker B speak at the same time for at most time_overlap range.

Successful interruption statistics (matrix) include: FUNCTION(number of successful interruptions) across interaction participants calculated during time interval T. A successful interruption is defined as speaker A is speaking, speaker B starts speaking, speaker A continues to speak but stops speaking after at least X seconds and speaker B continues to speak for at least Y seconds.

Unsuccessful interruption statistics (matrix) include: FUNCTION(number of unsuccessful interruptions) across interaction participants calculated during time interval T. An unsuccessful interruption is defined as speaker A is speaking, speaker B starts speaking but stops after at most Y seconds while speaker A continues to speak.

Dominance statistics include: FUNCTION(speaking time)/TOTAL(speaking time) calculated during time interval T for each interaction participant.

Mirroring statistics include: FUNCTION(speech/body movement features) across interaction participants calculated during time interval T.

1. For each length N segment within the session, determine if there is an interaction within the segment.
2. For all participants in the interaction, collect all data during the current segment.
   a. To analyze amplitude, consider only data collected during a speaking event within the segment. (Multiply amplitude vector by transpose of speech/nonspeech vector.)
   b. To analyze body movement energy, consider all samples within the interaction.
3. For each time series,
   a. Calculate the autocorrelation function. If the minimum value of the autocorrelation function is significant (less than 0.05/N), fit an autoregressive model to the data and retain the residuals. If the autocorrelation function does not have significant values at any lag, retain the original time series.
4. Compute cross-correlation for each pair of participants for lags from 1 to N−1.
5. Average the absolute values of the cross-correlation that are significant (outside the range 2N). These are the mirroring values.

Notes

A high value for the correlation between (x,y) at positive lags (as calculated using statsmodels package in Python)

represents x leading y—or y mirroring x. The values for x mirroring y are obtained by switching the order of the arguments in the function being used.

Large negative values for the cross-correlation between x and y are symbolic of the series for x being highly correlated with the inverse of y. Since this complementarity can be considered mirroring, we average the absolute values of the cross-correlation to compute the metric.

The AR model is fit by finding the order of the model that maximizes the Akaike Information Criterion.

The output for this metric is a list with timestamps and for each badge and a column with the mirroring values for each other person selected during the exported session.

Influence statistics include: FUNCTION(speech/body movement features)

This metric uses the idea of prediction to determine whether someone is influencing another person. One method of calculating influence that uses the idea of Granger causality would be:

Assume the maximum number of terms in the model p has been chosen by the user. For each value 1, . . . , p':

1. Create a model of person 1's data using ordinary least squares on only this person's data.

2. Repeat step 1 using ordinary least squares on data from person 1 AND person 2.

3. Compare the sum of squares error of the two models computed in steps 1 and 2. If (a) the error using the series derived in step 2 is significantly less than that obtained using the series from step 1 and (using a Chi-square test) (b) the terms in this series derived from person 2 are significantly different than 0 (using an F-test), person 1 is being influenced by person 2.

Thus embodiments compute four social signals for speech features as well as for body movement features: mirroring statistics, activity statistics, consistency statistics and/or influence statistics of participants as detailed above. And embodiments can calculate social network features of centrality, closeness, degree (of centrality) and cohesion of participants based on the corresponding turn-taking matrix of the participant.

5) Conversation Dynamics and Meeting Effectiveness Visualization

FIGS. 4-7 illustrate output visualizations 400, 500, 600, 700 supported by the following operations of server 60 (tool 100). Embodiments thus provide a visualization tool 100 that displays in real time the interactions and social dynamics among badge/device 50 users throughout a meeting. Embodiments may further employ mobile devices or other computer devices 60a, 60b (FIG. 8) in addition to server 60 operating tool 100. For non-limiting example, server 60 may provide output (e.g., visualizations 400, 500, 600, 700) to and/or operatively process with mobile or other computer devices 60a, 60b. End users of server 60 may thus use mobile/computer devices 60a, 60b to implement the functions and operations of tool 100 and/or to view the visualizations 400, 500, 600, 600. FIGS. 4-7 are illustrative where server 60 and mobile/computer devices 60a, 60b are generally referenced 60.

Figure 7:
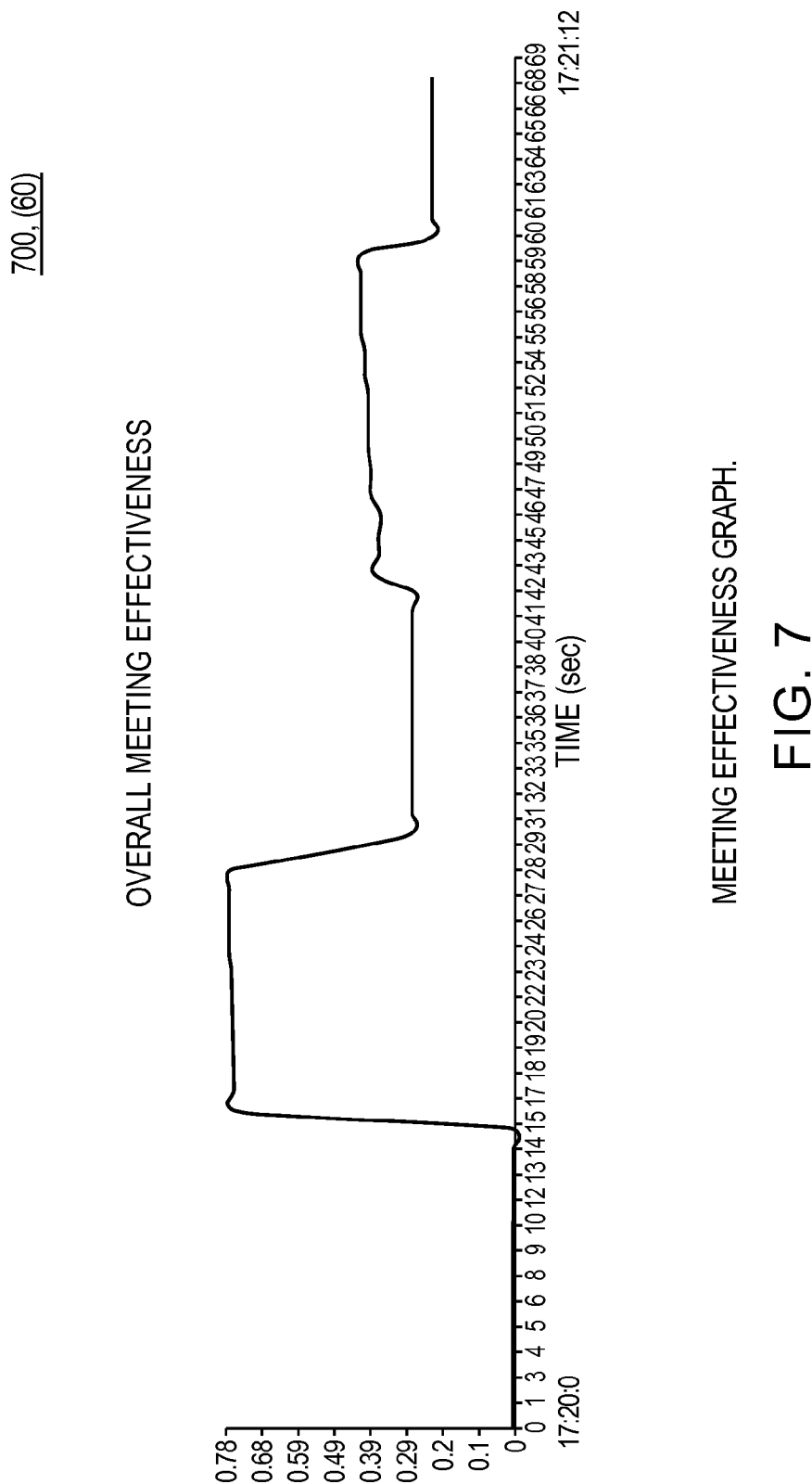

A participant's turn taking graph 500 (FIG. 5) represents the actual users by circles. A participation graph 600 (FIG. 6) shows a pie chart with the percentage of each user's speaking time. The meeting effectiveness graph 700 of FIG. 7 shows how effective the user's/participant's interactions are throughout the meeting Server 60 (tool 100) processing automatically detects the number of participants and draws one circle for each of them. The visualization 400 is updated according to:

a. Circles and names—Each user is depicted with 3 concentric circles with their names on top. The colored circle represents the actual user. The inner and outer dotted circles represent the minimum and maximum participation a user can attain.

b. Circle glow—Each user's circle glows whenever that particular participant speaks. For example, in FIG. 5 user B-784 is the only user speaking at that moment.

c. Interaction lines—The turn-taking graph 500 also shows the speaking turns taken between any two users by connecting their corresponding circles with a line. If there was a speech turn between user A and user B, then there would be a line between their two respective circles. The line thickness shows how intense was the interaction between those two users and is directly proportional to the number of speech turns between them normalized by the total number of turns across all participants (during a specified window of time, e.g. the most recent minute).

The participation graph 600 (FIG. 6) shows a user's "dominance score"=% (time that each person has been speaking)/(total speaking time without including silence) by accumulating all data received from the beginning of a real-time session. The collection of all participants' dominance scores shows participation balance. The proportion of each user on the pie chart 600 and the circle size in turn-taking graph 500 will be the same. For example, we can observe that user B-783 has spoken more than others in the meeting by just looking at the user's proportion in the pie chart 600. We can also see that the B-783 circle is the biggest of all in the turn-taking graph 500. Social network features of centrality, closeness, degree of centrality and cohesion of participants can be calculated based on the turn-taking (matrix) graph 500.

The meeting effectiveness graph 700 (FIG. 7) shows how effective the meeting was over a session. Meeting effectiveness calculation:

For each window W(t) (use the current second and the previous 59 seconds):

1. Find the maximum speaking time across participants (max of sum of speaking total of each user within the window).

2. Calculate speech overlap time within each window.

3. Calculate the number of turns/second for each participant (p) during the current window W(t).

$$\text{turns\_sec}(p) = (\text{sum of turns after each participant} - \text{self\_turns})/\text{window\_length};$$

4. Calculate the meeting effectiveness as:

$$\text{meeting\_effectiveness}(t) = [(\text{max\_speaking\_time} - \text{overlap\_time})/\text{window\_length} + \text{sum\_over all\_participants}(\text{abs}(\text{turns\_sec}(p) - \text{mean}(\text{turns\_sec}(p))))/(\text{mean}(\text{turns\_sec}(p))*\text{num\_participants})]/2$$

Thus embodiments output graphical displays or other screen views and indications of:

different participants in the conversation,
current participant speaking,
number of turns each participant has taken,
dominance of a participant,
turn duration of a given participant,
number of turns taken by the given or a certain participant,
number of turns taken before the given or certain participant,
number of turns taken after the given or certain participant,
number of self-turns taken by a participant (given or certain), turn-taking speed of a participant,
number of overlapping turns,
number of successful interruptions,
number of unsuccessful interruptions,
social signaling statistics of participants, and/or
participation balance of participants.

Different screen views and/or graphical renderings may illustrate various combinations of output information.

Real-Time Data Alignment Algorithm:

Since tool 100 runs in real time, it needs to get audio data from the Sociometric Badge/sensor 50 worn by each user. For simplicity let's assume every user is co-located in the same area/room. We also assume there is a centralized server 60 which collects data from all the badges/sensors 50 (via Bluetooth) and also runs the tool 100.

Once the badge data reaches the server 60, Applicant's Datalab software processes the data and stores it in a database. Then tool 100 queries the database periodically through a software API to get the required data to run the visualization 400.

Let's assume the meeting session starts at time 't' and goes for 'n' seconds. Tool 100 must start visualizing from second T until 't+n'. On the other hand, each sensor badge 50 has its own clock running inside and is likely to have a time drift between them even though they are synchronized. The sensor badge 50 sends the recorded audio amplitude with the timestamp and due to the abovementioned time difference, data arriving from each sensor badge 50 at the server 60 might have different timestamps. Also since we transfer data over Bluetooth, there could be some added latency in transmitting/receiving the data between server 60 and the sensor badge 50. Ultimately it comes down to the fact that we receive data from different badges 50 at different rates. This means the database might not have received all the most recent data that we query and hence return only what it has at that moment. Therefore, we need to make sure the data gets saved in proper order based on the timestamp from the badges 50.

One embodiment stores only the latest "window length" amount of amplitude data at any given time. Window length corresponds to the length of the window we would consider to compute the visualization metrics.

Algorithm:
1) Create an array of length "window length" W to store the audio amplitude
2) Query the database and get the data
3) Compare the latest timestamps of data from all the badges;
  a. Badge 50 data with the latest timestamp among all is the latest data received (meaning we will not have any data after this timestamp in this iteration)
  b. If it is the first iteration go to steps 4) and 5)
  c. Else shift all the arrays by the difference between the previous latest timestamp and the present latest timestamp (to make sure all the arrays are aligned)
4) Mark the last array index (window length−1) as holding the latest timestamp
5) Insert:
  a. Now iteratively insert data from all the badges in the array index corresponding to their timestamp
6) Repeat steps 2) to 5)

Real-Time Speech Detection Algorithm:
In this step we compute the threshold for each user to determine if the user is speaking or not.

Algorithm:
Like the amplitude array, we also maintain an array for speaking

1) Iterate through the amplitude array of each user
If speaking/not speaking has not been computed already for that index, then compute threshold
If the total seconds is greater than the window length, then consider the entire window for threshold, otherwise consider only the seconds for which we have received data
For each user:
  i. Compute the total of all the amplitude values
  ii. Compute mean amplitude
  iii. Compute standard deviation of the amplitude values (std)
  iv. Return the standard deviation as threshold
2) Find the maximum amplitude among the user for that array index
3) If (amplitude−mean amplitude) is greater than the threshold and if that amplitude is the maximum amplitude,
  Mark the user as speaking at that array index and increment total and individual speaking sum
4) Else
  Mark the user as not speaking at that array index Real-Time Turn-Taking Algorithm:
A turn is defined as the event in which a user speaks after another user within a given time window. If user A speaks after himself then it is considered as a self-turn to user A. If user A speaks after user B then it's considered as a turn between user A and user B.

Algorithm:
In order to compute turns in real time, tool 100 keeps track of both the window turns (considers only window length amount of data) and the overall turns (spanning all time from the beginning of a meeting).

1) Iterate the entire window length (i.e. from 0 to window length)
  a. If more than one user is speaking in the same second, increment overlap count
  b. For every user,
    i. If it is the first row of the window and if the user is speaking
      Increment window turns, turns matrix and overall turns matrix for the same user, self turns; continue to next user
    ii. If the user continues to speak (i.e. user speaks in the previous and present seconds); continue to next user
    iii. If user started speaking (i.e. if previous speaking value was 0 and the present value is 1)
      1. Loop through the silence window and see if anyone else has spoken within that window
      2. If yes,
        Increment window turns matrix and overall turns matrix between those two users; increment window turns,
      3. If no (it means same user has spoken in the silence window), increment window turns matrix and overall turns matrix for the same user; increment window turns and self turns At this point, we have all the necessary variables, arrays and matrices to produce the visualizations 400, 500, 600, 700 of FIGS. 4-7.

6) Sociometric DataLab Software (Conversation Analysis)

In the user interface of embodiments, a Data Export (or similar) window allows a user to indicate various detection (interaction) settings, resolutions and thresholds.

Descriptions of each setting parameter for one embodiment are given in the table below:

| Export setting | |
|---|---|
| Predefined settings | Choose "Small groups" if your study only lasted a few hours and involved 10 or fewer people, who were in proximity with each other throughout the experiment.<br>Choose "Large groups" if your study lasted more than a few hours, involved more than 10 people, who were not consistently in the vicinity of one another throughout the entire experiment.<br>Choose custom if you would like to adjust the settings for your own purposes. |
| Resolution | Resolution determines the time interval between timestamps on the exported spreadsheets.<br>For resolutions greater than the sampling frequency, data samples will be averaged over the resolution interval. For example: two consecutive values {1,0} at a resolution of is will become {.5} at a resolution of 2s.<br>For resolutions lower than the sampling frequency, data samples will be divided over equally over the resolution interval. For example: a value of {1} at a resolution of 1s will become {.5,.5} at a resolution of .5s |
| Interaction sources | |
| Face-to-face interactions | When this option is checked, DataLab will only run a speech and turn-taking analysis on badges when they are making face-to-face (infrared) detections of one another. |
| Proximity interactions | When this option is checked, DataLab will only run a speech and turn-taking analysis on badges when they are making in proximity (Bluetooth detections) of one another |
| Combined | When both options are combined, DataLab will combine face-to-face and proximity detections to determine when two badges were within conversation-distance of one another; and will only run a speech and turn-taking analysis on those time segments. |
| Face-to-face interactions | |
| Detection length | This setting is only relevant if Face-to-face interactions option is checked above. Detection length is the length of time after a face-to-face (infrared) detection, over which Data Lab will run a speech and turn-taking analysis |
| Proximity interactions | |
| Detection length | This setting is only relevant if Proximity interactions option is checked above. Detection length is the length of time after a proximity (Bluetooth) detection, over which Data Lab will run a speech and turn-taking analysis |
| RSSI Threshold | This setting is only relevant if Proximity interactions option is checked above. RSSI Threshold is the minimum RSSI (Received Signal Strength Indicator) of the Bluetooth detection, that DataLab will consider for running the speech and turn-taking analyses. |

The Data Export exports all data for a session on a single workbook containing multiple spreadsheets with the following formats:

1. Body Movement

Accelerometer data is collected at a sampling frequency of 20 Hz (by default). All values below are averages over the time resolution specified at the time of data export (see 4.5 Exporting Data and Analyses).

1.1. Body Movement 1.1.1. Body Movement (BM). Accelerometer's energy magnitude over the 3 axes of measurement.

| | Badge ID 1 | Badge ID 2 | ... | Badge ID k |
|---|---|---|---|---|
| Timestamp $t_0$ (MM/DD/YYYY hh:mm:ss.sss) | Accelerometer's energy for Badge ID 1 at $t_0$ | Accelerometer's energy for Badge ID 2 at $t_0$ | ... | Accelerometer's energy for Badge ID k at $t_0$ |
| . | . | . | ... | . |
| . | . | . | | . |
| . | . | . | | . |
| Timestamp $t_n$ | Accelerometer's energy for Badge ID 1 at $t_n$ | Accelerometer's energy for Badge ID 2 at $t_n$ | ... | Accelerometer's energy for Badge ID k at $t_n$ |

1.1.2. Activity (BM). Same format as the Body Movement (BM) spreadsheet. This is the absolute value of the first derivative of energy. This provides a more reliable measure of someone's activity, while eliminating the accelerometer's magnitude natural offset (since the accelerometer's magnitude when a badge is at rest is not exactly zero).

1.1.3. Rate (BM). Same format as the Body Movement (BM) spreadsheet. This is the second derivative of energy. The sign (positive or negative) of Rate (BM) indicates the direction of the change in someone's activity levels, as measured by Activity (BM). A positive Rate (BM) indicates the person's activity is increasing. A negative Rate (BM) indicates the activity is decreasing.

1.1.4. Consistency (BM). Same format as the Body Movement (BM) spreadsheet. This spreadsheet shows the consistency of each badge's activity, as measured by Activity (BM). Consistency ranges from 0 to 1, where 1 indicates no changes in activity level, and 0 indicates the maximum amount of variation in activity levels.

1.1.5. Mirroring (BM). This spreadsheet shows the amount of mirroring taking place between each back pair's activity levels. Mirroring (BM) values indicate how similar one badge's Activity (BM) data series is to another badge's Activity (BM) data series over time. The values range from 0 to 1, where 0 indicates no similarity and 1 indicates the two data series are identical. The format is as below:

| | Badge A | | | Badge B | | | Badge C |
|---|---|---|---|---|---|---|---|
| | Badge A | Badge B | Badge C | Badge A | Badge B | Badge C | ... |
| Timestamp (MM/DD/YYYY hh:mm:ss.sss) | NA | Badge A's mirroring of Badge B | Badge A's mirroring of Badge C | Badge B's mirroring of Badge A | NA | Badge B's mirroring of Badge C | ... |

1.2. Posture
1.2.1. Posture

|  | Badge ID 1 | | Badge ID 2 | |
| --- | --- | --- | --- | --- |
|  | Left-right | Front-back | Left-right | Front-back |
| Timestamp $t_0$ (MM/DD/YYYY hh:mm:ss.sss) | Orientation angle in the left-right plane for Badge ID 1 at Time $t_0$ | Orientation angle in the front-back plane for Badge ID 1 at Time $t_0$ | Orientation angle in the left-right plane Badge ID 2 at Time $t_0$ | Orientation angle in the front-back plane Badge ID 2 at Time $t_0$ |

1.2.2. Activity (Posture). Same format as the Body Movement (BM) spreadsheet. Activity (Posture) shows the absolute angular velocity for every badge at every timestamp.

1.2.3. Rate (Posture). Same format as the Body Movement (BM) spreadsheet. Rate (Posture) shows the angular acceleration for every badge at every timestamp.

1.2.4. Mirroring (Posture). This spreadsheet shows the amount of mirroring taking place between each back pair's postures. Mirroring (Posture) values indicate how similar one badge's Activity (Posture) data series is to another badge's Activity (Posture) data series over time. The values range from 0 to 1, where 0 indicates no similarity and 1 indicates the two data series are identical. The format is the same as the Mirroring (BM) spreadsheet.

2. Turn-Taking Analysis 2.1. Turn-Taking Analysis. Yields two spreadsheets, n_tt_turn-taking, and r_tt_turntaking. The first, n_tt_turntaking, shows a matrix of the number of turns each badge-wearer took after each other badge wearer:

|  | Badge A | Badge B | Badge C |
| --- | --- | --- | --- |
| Badge A | Number of times Badge A paused and then spoke again before anyone else spoke | Number of times Badge A spoke after Badge B | Number of times Badge A spoke after Badge C |
| Badge B | Number of times Badge B spoke after Badge A | Number of times Badge B paused and then spoke again before anyone else spoke | Number of times Badge B spoke after Badge C |
| Badge C | Number of times Badge C spoke after Badge A | Number of times Badge C spoke after Badge B | Number of times Badge C paused and then spoke again before anyone else spoke |

The second spreadsheet, r_tt_turntaking, shows the summary of turn-taking for each badge:

| Participant | # of turns | # of speaking segments | # of pauses | Average speaking segment length | Average pause length | Successful Interrupts | Unsuccessful Interrupts |
| --- | --- | --- | --- | --- | --- | --- | --- |
| Badge ID | Number of time the badge-wearer spoke after someone else. | A speech segment refers to one chunk of speaking time, whether it occurs after a pause in one's own speech or after someone else was speaking. | Number of pauses made by the badge-wearer. | Average length of each speaking segment. | Average length of each pause. | Number of successful interruptions made by the badge. | Number of unsuccessful interruptions made by the badge. |

2.2. Successful Interruptions. Matrix showing the number of times each badge successfully interrupted each other badge.

|  | Badge A | Badge B | Badge C |
| --- | --- | --- | --- |
| Badge A | 0 | Number of times Badge A successfully interrupted Badge B | Number of times Badge A successfully interrupted Badge C |
| Badge B | Number of times Badge B successfully interrupted Badge A | 0 | Number of times Badge B spoke after Badge C |
| Badge C | Number of times Badge C successfully interrupted Badge A | Number of times Badge C successfully interrupted Badge B | 0 |

2.3. Unsuccessful Interruptions Matrix showing the number of times each badge unsuccessfully interrupted each other badge. (Same format as Successful Interruptions above).

3. Speech Analysis

Audio data is sampled at a frequency of 8 kHz. The averages referred to below are computed over 1 second (configurable).

3.1. Speech Analysis 3.1.1. Speech profile. For every badge at each timestamp, this spreadsheet shows the amount of time (in seconds) each badge spent:

Speaking—the badge-wearer was speaking, and no one else was speaking

Overlapping—the badge-wearer was speaking at the same time as someone else

Listening—the badge-wearer was silent, and someone else was speaking

Silent—the badge-wearer was silent, and so were all other badge-wearers in his/her proximity Total_Speaking—the badge-wearer was speaking (regardless of whether or not anyone else was speaking) This measure combines Speaking and Overlapping.

Total_Silent—the badge-wearer was not speaking (regardless of whether or not anyone else was speaking) This measure combines Listening and Silent.

3.1.2. Dominance. For each timestamp, this spreadsheet shows how much each participant wearing a badge dominated a conversation with someone in his/her proximity.

3.2. Audio (front)

3.2.1. Activity (volume) (front)

|  | Badge ID 1 | Badge ID 2 | ... | Badge ID k |
|---|---|---|---|---|
| Timestamp $t_0$ (MM/DD/YYYY hh:mm:ss.sss) | Average absolute value of front amplitude for Badge ID 1 at $t_0$ | Average absolute value of front amplitude for Badge ID 2 at $t_0$ | ... | Average absolute value of front amplitude for Badge ID k at $t_0$ |
| . . . | . . . | . . . | . . . . | . . . |
| Timestamp $t_n$ | Average absolute value of front amplitude for Badge ID 1 at $t_n$ | Average absolute value of front amplitude for Badge ID 2 at $t_n$ | ... | Average absolute value of front amplitude for Badge ID k at $t_n$ |

3.2.2. Consistency (front). This spreadsheet shows the consistency of each badge's front audio amplitude, as measured in Activity (volume) (front). Consistency ranges from 0 to 1, where 1 indicates no changes in speech amplitude, and 0 indicates the maximum amount of variation in speech amplitude.

3.2.3. Dominant Frequency (front)

|  | Badge ID | | | | | | | |
|---|---|---|---|---|---|---|---|---|
|  | hz_0 | amp_0 | hz_1 | amp_1 | hz_2 | amp_2 | hz_3 | amp_3 |
| Timestamp (MM/DD/YYYY hh:mm:ss.sss) | frequency of the strongest peak in the frequency spectrum | amplitude of the strongest peak in the frequency spectrum | frequency of the $2^{nd}$ strongest peak in the frequency spectrum | amplitude of the $2^{nd}$ strongest peak in the frequency spectrum | $3^{rd}$ strongest peak | | $4^{th}$ strongest peak | |

Note: There are potentially 4 frequency bands shown, hz_0 & amp_0 is the strongest PEAK in cepstrum, hz_1 & amp_1 is the second strongest PEAK, and so on. If there are fewer than k peaks in cepstrum, the hz_k and larger values are empty. For instance, if there are only two peaks in cepstrum, hz_2 and hz_3 are empty and not exported.

3.2.4. Raw Mel Coefficients(t_audio_front_raw_mel1)

|  | Badge ID | | | | | | | | | | | |
|---|---|---|---|---|---|---|---|---|---|---|---|---|
|  | 0 | 1 | 2 | 3 | 4 | 5 | 6 | 7 | 8 | 9 | 10 | 11 |
| Timestamp (MM/DD/YYYY hh:mm:ss.sss) | Mel Coefficient for $0^{th}$ Mel band | Mel Coefficient for $1^{st}$ Mel band | Mel Coefficient for $2^{nd}$ Mel band | | | | | | | | | |

** See below for Mel band definitions

| Mel Band | Start Hz | End Hz |
|---|---|---|
| 0 | 0 | 199 |
| 1 | 74 | 345 |
| 2 | 199 | 514 |
| 3 | 345 | 711 |
| 4 | 514 | 939 |
| 5 | 711 | 1204 |
| 6 | 939 | 1512 |
| 7 | 1204 | 1870 |
| 8 | 1512 | 2286 |
| 9 | 1870 | 2769 |
| 10 | 2286 | 3330 |
| 11 | 2769 | 3983 |

3.2.5. Raw Spectrum Coefficients (front)

| | Badge ID | | | | | | | | | | | |
|---|---|---|---|---|---|---|---|---|---|---|---|---|
| | 0 | 1 | 2 | 3 | 4 | 5 | 6 | 7 | 8 | 9 | 10 | 11 |
| Timestamp (MM/DD/YYYY hh:mm:ss.sss) | Spectrum DC term | $1^{st}$ spectral coefficient | $2^{nd}$ spectral coefficient | | | | | | | | | |

** FFT size is 512 samples; Welch method; Hann Window 3.2.6. Raw Cepstrum Coefficients (front)

| | Badge ID | | | | | | | | | | | |
|---|---|---|---|---|---|---|---|---|---|---|---|---|
| | 0 | 1 | 2 | 3 | 4 | 5 | 6 | 7 | 8 | 9 | 10 | 11 |
| Timestamp (MM/DD/YYYY hh:mm:ss.sss) | $0^{th}$ cepstral coefficient | $1^{st}$ cepstral coefficient | $2^{nd}$ cepstral coefficient | | | | | | | | | |

**Calculated based on spectrum, and shares the same properties 3.2.7. Mirroring (volume) (front). This spreadsheet shows the amount of mirroring taking place between each back pair's speech amplitudes (volume). Mirroring (volume) values indicate how similar one badge's Activity (volume) data series is to another badge's Activity (volume) data series over time. The values range from 0 to 1, where 0 indicates no similarity and 1 indicates the two data series are identical. The format is the same as the Mirroring (BM) and Mirroring (Posture) spreadsheets.

3.2.8. Mirroring (f0) (front). This spreadsheet shows the amount of mirroring taking place between each back pair's speech dominant frequencies. Mirroring (f0) values indicate how similar one badge's hz_0 data from the Dominant Frequency (front) spreadsheet is to another badge's hz_0 data over time. The values range from 0 to 1, where 0 indicates no similarity and 1 indicates the two data series are identical. The format is the same as the Mirroring (BM) and Mirroring (Posture) spreadsheets.

3.3. Audio (back)

All audio back spreadsheets are the same as the Audio (front) spreadsheets, but show data collected from the back (rather than the front) microphone.

4. Interactions 4.1. Interactions 4.1.1. Combined. Combines Bluetooth and infrared detections to determine the number of seconds (within each time interval specified in the export resolution) that each badge was within interaction-distance of every other badge.

| | Badge A | | | Badge B | | | Badge C |
|---|---|---|---|---|---|---|---|
| | Badge A | Badge B | Badge C | Badge A | Badge B | Badge C | ... |
| Timestamp (MM/DD/YYYY hh:mm:ss.sss) | NA | Number of seconds Badge A was near Badge B | Number of seconds Badge A was near Badge C | Number of seconds Badge B was near Badge A | NA | Number of seconds Badge B was near Badge C | ... |

4.1.2. Proximity. Uses only Bluetooth detections to determine the number of seconds (within each time interval specified in the export resolution) that each badge was within interaction-distance of every other badge.

4.1.3. Face-to-face. Uses only infrared detections to determine the number of seconds (within each time interval specified in the export resolution) that each badge was within interaction-distance of every other badge.

4.1.4. Conversations. Shows the conversation that each badge-wearer was involved in at each timestamp. For example if A and B were involved in a conversation, and B and C were involved in a conversation soon after, the spreadsheet might look like this:

| Timestamp | Badge A | Badge B | Badge C |
|---|---|---|---|
| $t_0$ | 1 | 1 | 0 |
| $t_1$ | 1 | 1 | 0 |
| $t_2$ | 1 | 1 | 0 |
| $t_3$ | 0 | 0 | 0 |
| $t_4$ | 0 | 2 | 2 |
| $t_5$ | 0 | 2 | 2 |

4.1.5. Exploration score. This measure shows up in the summary spreadsheet.

4.2. Social Network (face-to-face)

4.2.1. Network Matrix (face-to-face). There are two Network Matrix (face-to-face) spreadsheets. The first, n_facetoface_matrix1, is a matrix showing the number of infrared detections each badge made of every other badge.

| | Badge A | Badge B | Badge C |
|---|---|---|---|
| Badge A | | Number times Badge A detected Badge B | Number of time Badge A detected Badge C |
| Badge B | Number of time Badge B detected Badge A | | Number of time Badge B detected Badge C |
| Badge C | Number of time Badge C detected Badge A | Number times Badge C detected Badge B | |

The second, r_facetoface_matrix1, shows all the infrared detections made over time. Note that although there is a column for RSSI values, RSSI (Received Signal Strength Indication) is only relevant for Bluetooth detections.

| | Badge ID | Other ID | RSSI |
|---|---|---|---|
| Timestamp $t_0$ (MM/DD/YYYY hh:mm:ss.sss) | Badge that made detection at $t_0$ | Badge detected | (always blank for face-to-face detections) |
| . | . | . | (always blank for face-to-face detections) |
| Timestamp $t_n$ | Badge that made detection at $t_n$ | Badge detected | (always blank for face-to-face detections) |

4.2.2. Betweenness centrality (face-to-face). This measure shows up in the summary spreadsheet (see Summary section below).

4.2.3. Closeness centrality (face-to-face). This measure shows up in the summary spreadsheet (see Summary section below).

4.2.4. Closeness vitality (face-to-face). This measure shows up in the summary spreadsheet (see Summary section below).

4.2.5. Cohesion (face-to-face). This measure shows up in the summary spreadsheet.

4.2.6. Degree centrality (face-to-face). This measure shows up in the summary spreadsheet (see Summary section below).

4.3. Social Network (proximity)

All Social Network (proximity) spreadsheets are the same as the Social Network (face-to-face), but show data from Bluetooth detections, rather than infrared detections.

5. Miscellaneous 5.1. Real time clock drift 5.2. Real time clock sync. Shows when the badge's internal clock was synchronized to that of your computer (which is pulled from online if you are connected to the internet), and shows the time difference between the badge's previous clock and the computer's clock.

5.3. Room temperature. Shows the room temperature for every badge at each timestamp.

5.4. Buttons. Shows the timestamp when various buttons/features were turned on/off and the value they were changed to ("on" or "off").

6. Summary

| | v = Badge ID k |
|---|---|
| accel_energy | average Accel energy for Badge k over the course of the session |
| accel_consistency | average Accel consistency for Badge k over the course of the session |
| audio_front_amplitude | average amplitude from the front microphone for Badge k over the course of the session |
| audio_front_consistency | average amplitude consistency from the front microphone for Badge k over the course of the session |
| audio_back_amplitude | average amplitude from the back microphone for Badge k over the course of the session |
| audio_back_consistency | average audio consistency from the back microphone for Badge k over the course of the session |
| ir_betweenness_centrality | the sum of the fraction of all-pairs shortest paths that pass through v (based on IR detections); normalized by $$\frac{1}{(n-1)(n-2)}$$ |
| ir_closeness_centrality | the inverse of the average distance to all other vertices (based on IR detections); normalized by $$\frac{n-1}{|E|-1}$$ where n is the number of vertices in the connected part of the graph; calculated for connected parts separately |
| ir_closeness_vitality | the change in the sum of distances between all vertex pairs when excluding v (based on IR detections) |
| ir_cohesion | a weighted measure of the number of transitive triads in which v participated during the session (based on IR detections) |
| ir_degree_centrality | the fraction of vertices to which v is connected |
| bt_betweenness_centrality | the sum of the fraction of all-pairs shortest paths that pass through v (based on IR detections); normalized by $$\frac{1}{(n-1)(n-2)}$$ |
| bt_closeness_centrality | the inverse of the average distance to all other vertices (based on IR detections); normalized by |

-continued

| | |
|---|---|
| v = Badge ID k | |
| $\frac{n-1}{\|E\|-1}$ | where n is the number of vertices in the connected part of the graph; calculated for connected parts separately |
| bt_closeness_vitality | the change in the sum of distances between all vertexpairs when excluding v (based on IR detections) |
| bt_cohesion | a weighted measure of the number of transitive triads in which v participated during the session (based on IR detections) |
| bt_degree_centrality | the fraction of vertices to which vis connected |

While this invention has been particularly shown and described with references to example embodiments thereof, it will be understood by those skilled in the art that various changes in form and details may be made therein without departing from the scope of the invention encompassed by the appended claims.

What is claimed is:

1. A computer-based method of measuring group conversation dynamics comprising:
   determining existence of respective conversations between two or more people, said determining including obtaining speech audio and body movement sensor data corresponding to each person, and from the obtained speech audio and body movement sensor data, defining start time and end time of each conversation, detecting number of participants in each conversation, and identifying participants involved in each conversation, wherein the speech audio and body movement sensor data is obtained from a wearable electronic sensor;
   from a stream of speech audio sensor data corresponding to a determined conversation, identifying participants' portions of the speech audio data as speech or silence;
   as a function of the identified speech and silence of participants in the determined conversation, detecting turn-taking among the participants in the determined conversation;
   from a stream of body movement sensor data corresponding to the determined conversation, identifying changes in body posture of the participants in the determined conversation;
   based on the obtained speech audio and body movement sensor data, calculating non-linguistic social signaling statistics of one of the participants; and
   outputting indications of said one participant's turns taken in the determined conversation.

2. A method as claimed in claim 1 wherein said detecting turn taking includes determining per participant:
   turn duration,
   number of turns,
   turn-taking speed (e.g., number of turns per unit of time), and
   number of overlapping turns.

3. A method as claimed in claim 1 wherein said detecting turn taking includes determining for a participant:
   number of turns taken before this participant,
   number of turns taken after this participant,
   number of self-turns taken by this participant,
   number of speaking segments,
   number of pauses,
   average speaking segment length, and
   average pause length.

4. The method as claimed in claim 1 wherein said detecting turn taking includes determining number of successful interruptions and number of unsuccessful interruptions.

5. The method as claimed in claim 1 further comprising:
   based on the identified speech or silence, calculating dominance statistics of a participant.

6. The method as claimed in claim 1 wherein calculating non-linguistic social signaling statistics includes calculating mirroring statistics, activity statistics, consistency statistics or influence statistics of the one participant.

7. The method as claimed in claim 1 further comprising:
   from the speech audio sensor data, collecting speech feature data corresponding to the participants, the speech features including any of speech volume and speech fundamental frequency; and
   wherein the calculating is further based on the collected speech feature data, the identified changes in body posture, and the identified speech and silence of the one participant.

8. The method as claimed in claim 7 wherein calculating non-linguistic social signaling statistics of the one participant includes calculating mirroring statistics, activity statistics, consistency statistics or influence statistics for the speech features and the body movement sensor data.

9. The method as claimed in claim 1 further comprising:
   based on the obtained speech audio and body movement sensor data, calculating social network statistics of a participant including centrality, closeness, and cohesion.

10. The method as claimed in claim 1 wherein outputting indications includes rendering a graphical display illustrating in real-time any combination of:
    different participants in the conversation,
    current participant speaking,
    number of turns each participant has taken, and
    dominance of a participant in the conversation.

11. The method as claimed in claim 10 wherein dominance is calculated as a percentage of total non-silence time that the participant has been speaking.

12. The method as claimed in claim 1 wherein outputting indications includes rendering displays illustrating any combination of:
    turn duration of a given participant,
    number of turns taken by a certain participant,
    number of turns taken before the certain participant,
    number of turns taken after the certain participant,
    number of self-turns taken by the certain participant,
    turn-taking speed of a participant,
    number of overlapping turns,
    number of successful interruptions,
    number of unsuccessful interruptions,
    social signaling statistics of participants, and
    participation balance of participants.

13. The method as claimed in claim 10 wherein the graphical display further comprises a visualization of meeting effectiveness.

14. A data processing system measuring group conversation dynamics, comprising:
    a processor configured to:
      determine existence of respective conversations between two or more people, including obtaining speech audio and body movement sensor data corresponding to each person, and from the obtained speech audio and body movement sensor data, define start time and end time of each determined conversation, detect number of participants in each conversation, and identify participants involved in each determined conversation, wherein the speech audio and body movement sensor data is obtained from a wearable electronic sensor;

from a stream of speech audio sensor data corresponding to a determined conversation, identify participants' portions of the speech audio data as speech or silence;

as a function of the identified speech and silence of participants in the determined conversation, detect turn-taking among the participants in the conversation;

from a stream of body movement sensor data corresponding to the determined conversation, identify changes in body posture of the participants in the determined conversation;

based on the obtained speech audio and body movement sensor data, calculate non-linguistic social signaling statistics of one of the participants; and a display subsystem coupled to the processor and outputting indications of said one participant's turns taken in the conversation.

15. A data processing system as claimed in claim 14 wherein the processor detecting turn-taking includes determining per participant:
   turn duration,
   number of turns,
   turn-taking speed, and
   number of overlapping turns; and
   determining number of successful and unsuccessful interruptions.

16. A data processing system as claimed in claim 14 wherein the processor detecting turn-taking includes determining for a participant:
   number of turns taken before this participant,
   number of turns taken after this participant,
   number of self-turns taken by this participant,
   number of speaking segments,
   number of pauses,
   average speaking segment length, and
   average pause length.

17. A data processing system as claimed in claim 14 wherein the processor further:
   based on the identified speech or silence, calculates dominance statistics of a participant.

18. A data processing system as claimed in claim 14 wherein non-linguistic social signaling statistics includes mirroring statistics, activity statistics, consistency statistics or influence statistics of the one participant.

19. A data processing system as claimed in claim 14 wherein the processor is further configured to:
   based on the obtained speech audio and body movement sensor data, calculate social network statistics of a participant including centrality, closeness, and cohesion.

20. A data processing system as claimed in claim 14 wherein the display subsystem outputting indications includes rendering a graphical display illustrating in real-time any combination of:
   different participants in the conversation,
   current participant speaking,
   number of turns each participant has taken, and
   dominance of a participant in the conversation.

21. A data processing system as claimed in claim 20 wherein dominance is calculated as a percent of total non-silence time that the participant has been speaking.

22. A data processing system as claimed in claim 14 wherein the display subsystem renders displays illustrating any combination of:
   turn duration of a given participant,
   number of turns taken by a certain participant,
   number of turns taken before the certain participant,
   number of turns taken after the certain participant,
   number of self-turns taken by the certain participant,
   turn-taking speed of a participant,
   number of overlapping turns,
   number of successful interruptions,
   number of unsuccessful interruptions,
   social signaling statistics of participants, and
   participation balance of participants.

23. A data processing system as claimed in claim 14 wherein the display subsystem renders a graphical display that comprises a visualization of meeting effectiveness.

24. The method as claimed in claim 1 wherein the determining further includes obtaining proximity sensor data, and the number of participants in each conversation is detected from a combination of the proximity sensor data, the speech audio sensor data, and the body movement sensor data.

25. A data processing system as claimed in claim 14 wherein the processer determining further includes obtaining proximity sensor data, and the processor detects number of participants in each conversation from a combination of the proximity sensor data, the speech audio sensor data, and the body movement sensor data.

26. A computer-based method of measuring group conversation dynamics comprising:
   determining existence of respective conversations between two or more people, said determining including obtaining speech audio and body movement sensor data corresponding to each person, and from the obtained speech audio and body movement sensor data, defining start time and end time of each conversation, detecting number of participants in each conversation, and identifying participants involved in each conversation, wherein the speech audio and body movement sensor data is obtained from a wearable electronic sensor;
   from a stream of speech audio sensor data corresponding to a determined conversation, identifying participants' portions of the speech audio data as speech or silence;
   as a function of the identified speech and silence of participants in the determined conversation, detecting turn-taking among the participants in the determined conversation;
   from a stream of body movement sensor data corresponding to the determined conversation, identifying changes in body posture of the participants in the determined conversation; and
   based on the obtained speech audio and body movement sensor data, calculating non-linguistic social signaling statistics of one of the participants.

27. The method as claimed in claim 26 further including outputting indications of said one participant's turns taken in the conversation, wherein outputting indications includes rendering a graphical display illustrating in real-time any combination of:
   different participants in the conversation,
   current participant speaking,
   number of turns each participant has taken, and
   dominance of a participant in the conversation.

* * * * *